United States Patent
Kim et al.

(10) Patent No.: US 12,293,833 B2
(45) Date of Patent: May 6, 2025

(54) HEART CONDITION DETECTION SENSOR DEVICE AND SYSTEM FOR PROVIDING COMPLEX LIFE SUPPORT SOLUTION USING SAME

(71) Applicant: Korea University Research and Business Foundation, Seoul (KR)

(72) Inventors: Dong Joo Kim, Seoul (KR); Young Tak Kim, Nonsan-si (KR); Hyun Ji Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 239 days.

(21) Appl. No.: 18/008,266

(22) PCT Filed: Jun. 11, 2021

(86) PCT No.: PCT/KR2021/007339
§ 371 (c)(1),
(2) Date: Dec. 5, 2022

(87) PCT Pub. No.: WO2021/251796
PCT Pub. Date: Dec. 16, 2021

(65) Prior Publication Data
US 2023/0282352 A1    Sep. 7, 2023

(30) Foreign Application Priority Data

Jun. 12, 2020 (KR) .................. 10-2020-0071654
Aug. 27, 2020 (KR) .................. 10-2020-0108603
Aug. 27, 2020 (KR) .................. 10-2020-0108604

(51) Int. Cl.
*G16H 50/20* (2018.01)
*G16H 40/67* (2018.01)
*G16H 40/20* (2018.01)

(52) U.S. Cl.
CPC ............. *G16H 50/20* (2018.01); *G16H 40/67* (2018.01); *G16H 40/20* (2018.01)

(58) Field of Classification Search
CPC ......... G16H 50/00; G16H 40/67; G16H 40/20
(Continued)

(56) References Cited

U.S. PATENT DOCUMENTS 10,194,821 B2 *   2/2019  Habte .................... A61B 5/352
2011/0190650 A1 * 8/2011  McNair ................ A61B 5/6898
                                                       600/518
(Continued)

FOREIGN PATENT DOCUMENTS

KR   10-2006-0117546 A   11/2006
KR   10-2014-0063100 A    5/2014
(Continued)

*Primary Examiner* — Michael Tomaszewski
(74) *Attorney, Agent, or Firm* — NSIP Law

(57) ABSTRACT

The present invention relates to a technical idea of monitoring a heart condition by analyzing biosignals measured using a sensor device for detecting a heart condition. In a method of monitoring a heart condition according to one embodiment of the present invention, electrocardiogram signals are measured from a user, feature information is extracted by performing machine learning of the time domain of the measured electrocardiogram signals, a plurality of cardiac abnormality type models are determined by performing machine learning of the extracted feature information, classification accuracy for the determined cardiac abnormality type models is calculated, and a cardiovascular disease of the user is determined using the determined cardiac abnormality type models and public cardiovascular disease data based on the calculated accuracy. That is, the present invention relates to a technique for assisting medical diagnosis.

20 Claims, 14 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 2016/0120431 A1* | 5/2016 | Habte | ................... | A61B 5/0245 |
| | | | | 600/509 |
| 2016/0183812 A1* | 6/2016 | Zhang | ...................... | G07C 9/37 |
| | | | | 600/301 |
| 2016/0287177 A1* | 10/2016 | Huppert | ............... | A61B 5/4839 |
| 2021/0193291 A1* | 6/2021 | Blake | ...................... | G16H 50/50 |
| 2022/0028060 A1* | 1/2022 | Masuda | ................. | G16H 40/67 |
| 2022/0384014 A1* | 12/2022 | Sarkar | ..................... | A61B 5/352 |
| 2023/0326601 A1* | 10/2023 | Xue | ........................ | A61B 5/346 |
| | | | | 600/523 |
| 2024/0188876 A1* | 6/2024 | Ghose | ................... | A61B 5/335 |

FOREIGN PATENT DOCUMENTS

| | | |
|---|---|---|
| KR | 10-1534131 B1 | 7/2015 |
| KR | 10-2017-0064960 A | 6/2017 |
| KR | 10-2018-0063440 A | 6/2018 |

\* cited by examiner

100

420

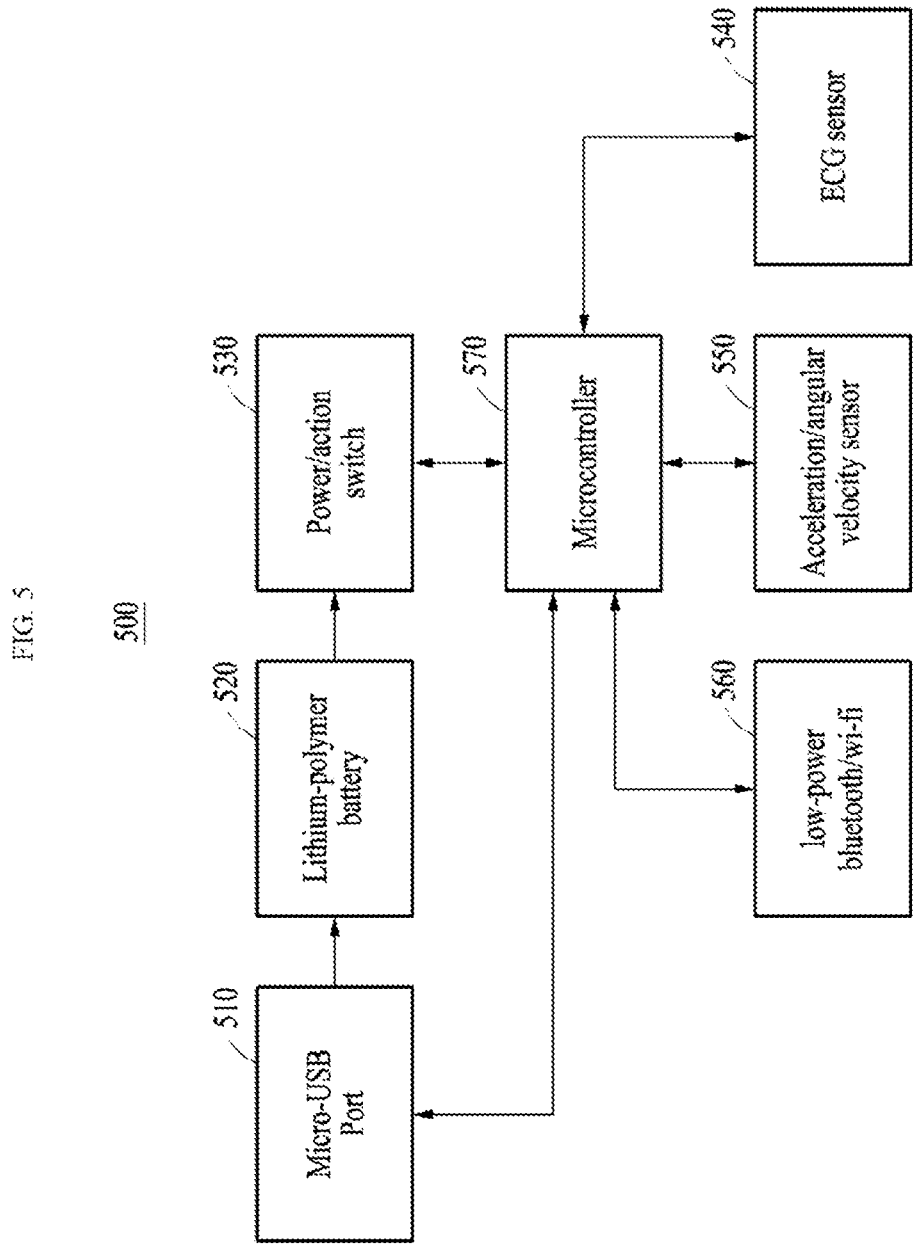

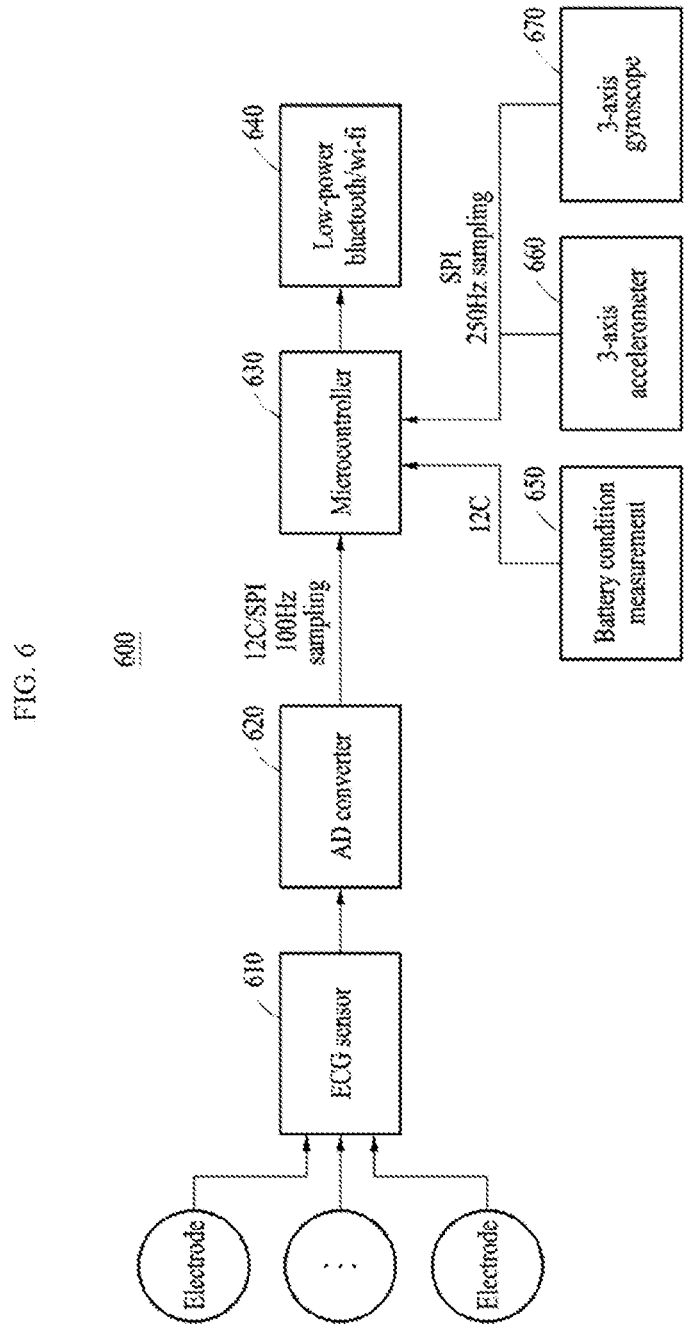

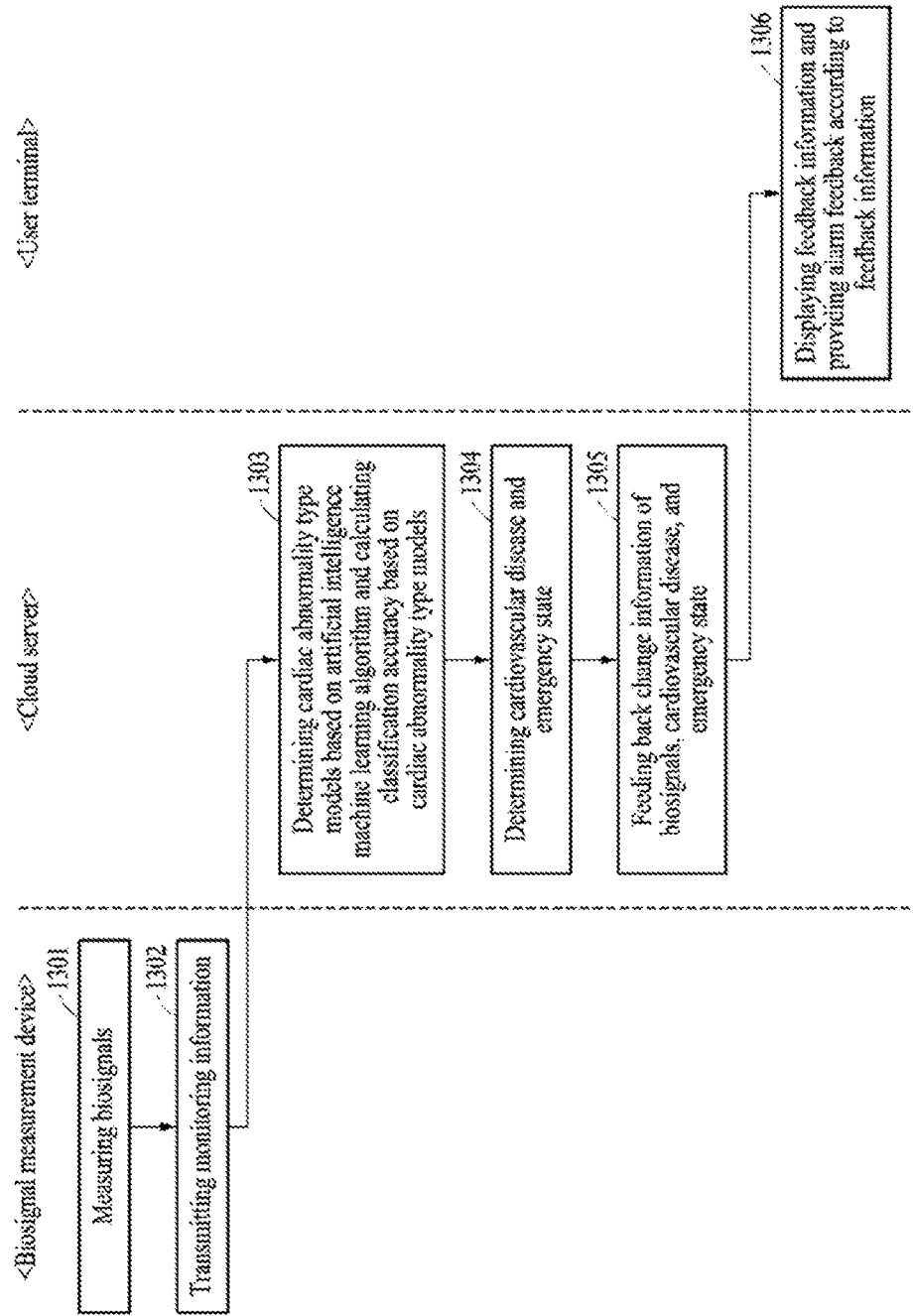

HEART CONDITION DETECTION SENSOR DEVICE AND SYSTEM FOR PROVIDING COMPLEX LIFE SUPPORT SOLUTION USING SAME

CROSS REFERENCE TO RELATED APPLICATIONS

This application is a U.S. National Stage Application of International Application No. PCT/KR2021/007339 filed on Jun. 11, 2021, which claims the benefit under 35 USC 119(a) and 365(b) of Korean Patent Application No. 10-2020-0071654, filed on Jun. 12, 2020 and Korean Patent Application Nos. 10-2020-0108603 and 10-2020-0108604 filed on Aug. 27, 2020, in the Korean Intellectual Property Office, the entire disclosure of which are incorporated herein by reference for all purposes.

TECHNICAL FIELD

The present invention relates to a technical idea for providing a life support complex solution by monitoring a heart condition by analyzing biosignals measured using a sensor device for detecting a heart condition or by monitoring and analyzing, based on artificial intelligence, biosignals measured using a biosignal measurement device. More particularly, the present invention relates to a technique for determining a cardiac abnormality type model by learning and analyzing, using an artificial intelligence algorithm, biosignals measured using a sensor device for detecting a heart condition and accurately determining a cardiovascular disease based on evaluation of the determined cardiac abnormality type model.

BACKGROUND ART

Referring to demographics, by 2025, the population over the age of 65 will be 10.50 million 8 thousand, accounting for 20% of the total population of 56.21 million. In addition, due to exponential increase in the number of critically ill patients, the capacity of nursing hospitals and nursing facilities is continuously increasing.

Cardiovascular and cerebrovascular diseases account for 24.3% of all deaths and have a direct correlation with aging.

According to information released by hospitals, the in-hospital mortality rate for critically ill patients is 18%, which is about twice that of developed countries, and one-third of all deaths in the country in 2018 are deaths in elderly care hospitals and nursing facilities.

Intensive care units that have attained grade 2 or higher in the adequacy assessment account for only about one-third of all intensive care units. The quality of health care services needs to be improved. In 2016, the proportion of medical expenses for hospitalization for the elderly was about 47.6%, and about 14% of the elderly population used about half of the total medical expenses.

The low profit of intensive care units contributes to the deficit of general hospitals. Among medical institutions, nursing hospitals make a significant contribution to job creation, but have the lowest inpatient income per 100 beds.

In terms of patient monitoring, representative techniques for solving the above problems include electrocardiogram (ECG), photoplethysmogram (PPG), a physical activity measurement system (Actigraph), and a monitoring technique using a 3D depth camera.

In terms of AI-based physiological signal processing, artifact removal related to deep-learning models, signal encoding and decoding related to deep-learning models, arrhythmia detection and classification related to deep-learning models, and risk assessment of chronic diseases related to deep-learning models are included.

In addition, in terms of general signal analysis, heart rate variability (HRV), baroreflex sensitivity (BRS), and pulse morphology analysis are included. In terms of edge computing, centralized monitoring of hospitals, an embedded artificial intelligence model, and real-time stream data analysis are included.

However, in the current technology for monitoring a patient in a ward, during monitoring of a patient in an intensive care unit, a false alarm occurs very frequently due to low-quality biosignal data, thereby deteriorating the work efficiency of medical staff and the prognosis of the patient.

In addition, medical data is doubling every 73 days until 2020, but labor-intensive and retrospective analysis is required to process large amounts of low-quality data.

In addition, compared to rapidly increasing data, there are not enough manpower to analyze data, but it is difficult to increase the medical manpower due to revenue problems.

DISCLOSURE

Technical Problem

Therefore, the present invention has been made in view of the above problems, and it is one object of the present invention to determine a classification model for major cardiovascular diseases such as myocardial infarction and coronary artery diseases based on a sensor device for detecting a heart condition that is attached to a patient and detects the heart condition of the patient, biosignals related to a heart condition, and a server using artificial intelligence algorithm and to prevent misdiagnosis by doctors and occurrence of false alarms based on the determined major cardiovascular disease classification model.

It is another object of the present invention to provide a heart condition monitoring system based on IoT and artificial intelligence for elderly patient management through real-time monitoring of patient's multimodal biosignals measured by a sensor device for detecting a heart condition that is attached to a patient and detects the heart condition of the patient.

It is still another object of the present invention to provide a sensor device for detecting a heart condition that detects the heart condition of a patient for heart condition analysis for real-time arrhythmia detection, biosignal quality management to improve signal analysis reliability, and assessment of major cardiovascular diseases for early disease management.

It is still another object of the present invention to detect major cardiac abnormalities such as tachycardia, bradycardia, atrial fibrillation, left bundle branch block, right bundle branch block, premature atrial contraction, premature ventricular contraction, and cardiac arrest by analyzing, based on a pre-stored artificial intelligence algorithm, biosignals measured by a sensor device for detecting a heart condition that is attached to a patient and detects the heart condition of the patient.

It is still another object of the present invention to improve the measurement accuracy of biosignals measured by a sensor device for detecting a heart condition that is attached to a patient and detects the heart condition of the patient by learning and evaluating the measurement accuracy of the biosignals by calculating cardiac dysfunction classification accuracy, emergency state classification accuracy, and artifact signal detection accuracy using a pre-stored artificial intelligence algorithm and an open data set.

It is still another object of the present invention to contribute to diagnosis assistance and reduction of medical costs through continuous monitoring of arrhythmias.

It is still another object of the present invention to reduce the number of false alarms occurring in a ward by accurately measuring and analyzing the current condition of a patient and improve the work efficiency of medical staff and the prognosis of a patient.

It is still another object of the present invention to provide a function for evaluating the risk of chronic diseases through analysis of pulse waves and electrocardiogram waveforms using an artificial intelligence learning technique.

It is still another object of the present invention to provide a life support complex solution including a telemedicine service in preparation for the post-corona era.

It is yet another object of the present invention to provide a life support complex solution that transmits emergency information and basic biosignal information to medical staff and emergency centers of nursing hospitals when an emergency such as cardiac arrest or a fall accident is detected, allows external organizations to receive analysis data in real time, and prepares for emergency states of applicants.

Technical Solution

In accordance with one aspect of the present invention, provided is a server including a monitoring information collector for collecting monitoring information including biosignals including electrocardiogram signals measured from a user; a signal extractor for extracting the electrocardiogram signals included in the collected monitoring information; an artificial intelligence processor for extracting morphological information as feature information by converting the extracted electrocardiogram signals into a time-standardized image based on a pre-stored artificial intelligence machine learning algorithm, determining a plurality of cardiac abnormality type models using the extracted feature information, calculating classification accuracy for the determined cardiac abnormality type models, and determining a cardiovascular disease of the user using the determined cardiac abnormality type models and public cardiovascular disease data based on the calculated accuracy; and a controller for controlling to provide the determined cardiovascular disease to a user terminal.

The artificial intelligence processor may generate a normalized signal based on a time domain of the extracted electrocardiogram signals, may convert the generated normalized signal into the time-standardized image, may generate a compressed signal by applying the pre-stored artificial intelligence machine learning algorithm-based weight to the converted image, may generate a reconstructed signal from the compressed signal using the applied weight, and may extract morphological information of the electrocardiogram signals as the feature information by performing machine learning of the weight so that a difference between the generated normalized signal and the generated reconstructed signal falls within a preset threshold range.

The artificial intelligence processor may perform machine learning of the feature information to determine the cardiac abnormality type models as at least one model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

The artificial intelligence processor may use an open data set, at least one model of the tachycardia model, the bradycardia model, the atrial fibrillation model, the left bundle branch block model, the right bundle branch block model, the premature atrial contraction model, and the premature ventricular contraction model, and the normal heart condition model to classify a true positive (TP) case in which cardiac abnormality is classified as the cardiac abnormality, a false negative (FN) case in which the cardiac abnormality is classified as normal, a false positive (FP) case in which the normal is classified as the cardiac abnormality, and a true negative (TN) case in which the normal is classified as the normal, and may calculate classification accuracy for at least one of the tachycardia model, the bradycardia model, the atrial fibrillation model, the left bundle branch block model, the right bundle branch block model, the premature atrial contraction model, and the premature ventricular contraction model based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

The artificial intelligence processor may use an open data set, the cardiac arrest model, and the normal heart condition model to classify a true positive (TP) case in which a cardiac arrest section is classified as the cardiac arrest section, a false negative (FN) case in which the cardiac arrest section is classified as a normal section, a false positive (FP) case in which the normal section is classified as the cardiac arrest section, and a true negative (TN) case in which the normal section is classified as the normal section, and may calculate emergency state classification accuracy based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

The artificial intelligence processor may classify a true positive (TP) case in which an artifact signal is classified as the artifact signal, a false negative (FN) case in which the artifact signal is classified as a normal signal, a false positive (FP) case in which the normal signal is classified as the artifact signal, and a true negative (TN) case in which the normal signal is classified as the normal signal, and may calculate artifact removal accuracy based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

After the electrocardiogram signals are measured, the controller may calculate the number of the measured electrocardiogram signals and the number of the measured motion signals and compare the calculated number of the electrocardiogram signals and the calculated number of the motion signals with a threshold value to confirm data reception states of the electrocardiogram signals and the motion signals.

The user terminal may provide an analysis result related to the determined cardiovascular disease through a display.

In accordance with another aspect of the present invention, provided is a sensor device for detecting a heart condition including a biosignal monitor for measuring biosignals including electrocardiogram signals from a user and outputting monitoring information including the measured biosignals through an artificial intelligence encoder; and an artificial intelligence processor for extracting electrocardiogram signals included in the output monitoring information, extracting morphological information as feature information by converting the extracted electrocardiogram signals into a time-standardized image based on a pre-stored artificial intelligence machine learning algorithm, determining a plurality of cardiac abnormality type models using the extracted feature information, calculating classification accuracy for the determined cardiac abnormality type models, and determining a cardiovascular disease of the user using the determined cardiac abnormality type models and public cardiovascular disease data based on the calculated accuracy.

The artificial intelligence processor may simulate data traffic generated when measuring the electrocardiogram signals, and may determine an operating state of the sensor device for detecting a heart condition based on the simulation.

The artificial intelligence processor may perform machine learning of the feature information to determine the cardiac abnormality type models as at least one model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

The biosignal monitor may further measure at least one of a motion signal and a body temperature signal from the user, and may output monitoring information further including the motion signal and the body temperature signal through an artificial intelligence encoder.

The artificial intelligence processor may detect emergency states including cardiac arrest and a fall of the user based on the measured electrocardiogram signals and the measured motion signals.

In accordance with still another aspect of the present invention, provided is a method of monitoring a heart condition including a step of measuring electrocardiogram signals from a user by the sensor device for detecting a heart condition; a step of extracting, by the server, morphological information as feature information by converting the measured electrocardiogram signals into a time-standardized image; a step of determining, by the server, a plurality of cardiac abnormality type models by performing machine learning of the extracted feature information; a step of calculating classification accuracy for the determined cardiac abnormality type models by the server; and a step of determining, by the server, a cardiovascular disease of the user using the determined cardiac abnormality type models and public cardiovascular disease data based on the calculated accuracy.

In accordance with still another aspect of the present invention, provided is a system for providing a life support complex solution including a gateway for transmitting monitoring information including biosignals including at least one of an electrocardiogram signal, a motion signal, a body temperature signal, and a pulse wave signal of an applicant to a server; and a server for extracting electrocardiogram signals of the biosignals from the transmitted monitoring information, extracting morphological information as feature information by converting the extracted electrocardiogram signals into a time-standardized image based on a pre-stored artificial intelligence machine learning algorithm, determining a plurality of cardiac abnormality type models using the extracted feature information, calculating classification accuracy for the determined cardiac abnormality type models, determining a cardiovascular disease of the applicant and whether the applicant is in an emergency state using the determined cardiac abnormality type models and public cardiovascular disease data based on the calculated accuracy, and feeding back information about the determined cardiovascular disease and whether the applicant is in an emergency state and change information of the biosignals to a user terminal.

The user terminal may include at least one of a medical staff terminal, a guardian terminal, and an emergency center terminal, the user terminal may output at least one of information about the determined cardiovascular disease and whether the applicant is in an emergency state and change information of the biosignals, and prescription information generated according to information output to the medical staff terminal may also be updated in the guardian terminal and the emergency center terminal.

Based on information about the determined cardiovascular disease and whether the applicant is in an emergency state and change information of the biosignals, the user terminal may provide at least one of a nursing management service, a disease data management service, a disease data visualization service, a disease data statistical service, and an emergency push notification service of the applicant.

In accordance with yet another aspect of the present invention, provided is a method of operating a system for providing a life support complex solution including a step of measuring, by a biosignal measurement device, biosignals including at least one of an electrocardiogram signal, a motion signal, a body temperature signal, and a pulse wave signal from an applicant; a step of transmitting, by the biosignal measurement device, monitoring information including the measured biosignals to a server through a gateway; a step of extracting, by the server, electrocardiogram signals of the biosignals from the transmitted monitoring information and extracting morphological information as feature information by converting the extracted electrocardiogram signals into a time-standardized image based on a pre-stored artificial intelligence machine learning algorithm; a step of determining, by the server, a plurality of cardiac abnormality type models using the extracted feature information; a step of calculating classification accuracy for the determined cardiac abnormality type models by the server; a step of determining, by the server, a cardiovascular disease of the applicant and whether the applicant is in an emergency state using the determined cardiac abnormality type models and public cardiovascular disease data based on the calculated accuracy; and a step of feeding back, by the server, information about the determined cardiovascular disease and whether the applicant is in an emergency state and change information of the biosignals to a user terminal.

Advantageous Effects

The present invention can determine a classification model for major cardiovascular diseases such as myocardial infarction and coronary artery diseases based on a sensor device for detecting a heart condition that is attached to a patient and detects the heart condition of the patient, biosignals related to a heart condition, and a server using artificial intelligence algorithm and prevent misdiagnosis by doctors and occurrence of false alarms based on the determined major cardiovascular disease classification model.

The present invention can provide a heart condition monitoring system based on IoT and artificial intelligence for elderly patient management through real-time monitoring of patient's multimodal biosignals measured by a sensor device for detecting a heart condition that is attached to a patient and detects the heart condition of the patient.

The present invention can provide a sensor device for detecting a heart condition that detects the heart condition of a patient for heart condition analysis for real-time arrhythmia detection, biosignal quality management to improve signal analysis reliability, and assessment of major cardiovascular diseases for early disease management.

The present invention can detect major cardiac abnormalities such as tachycardia, bradycardia, atrial fibrillation, left bundle branch block, right bundle branch block, premature atrial contraction, premature ventricular contraction, and cardiac arrest by analyzing, based on a pre-stored artificial intelligence algorithm, biosignals measured by a sensor device for detecting a heart condition that is attached to a patient and detects the heart condition of the patient.

The present invention can improve the measurement accuracy of biosignals measured by a sensor device for detecting a heart condition that is attached to a patient and detects the heart condition of the patient by learning and evaluating the measurement accuracy of the biosignals by calculating cardiac dysfunction classification accuracy, emergency state classification accuracy, and artifact signal detection accuracy using a pre-stored artificial intelligence algorithm and an open data set.

The present invention can contribute to diagnosis assistance and reduction of medical costs through continuous monitoring of arrhythmias.

The present invention can reduce the number of false alarms occurring in a ward by accurately measuring and analyzing the current condition of a patient, and thus can improve the work efficiency of medical staff and the prognosis of a patient.

The present invention can provide a function for evaluating the risk of chronic diseases through analysis of pulse waves and electrocardiogram waveforms using an artificial intelligence learning technique.

The present invention can provide a life support complex solution including a telemedicine service in preparation for the post-corona era.

The present invention can provide a life support complex solution that transmits emergency information and basic biosignal information to medical staff and emergency centers of nursing hospitals when an emergency such as cardiac arrest or a fall accident is detected, and allow external organizations to receive analysis data in real time, and prepares for emergency states of applicants.

DESCRIPTION OF DRAWINGS

FIG. 5 is a diagram for explaining the additional components of a sensor device for detecting a heart condition according to one embodiment of the present invention.

FIG. 6 is a diagram for explaining the flow of major events of biosignal measurement and data transmission according to one embodiment of the present invention.

FIG. 13 is a diagram for explaining a method of operating a system for providing a life support complex solution according to one embodiment of the present invention.

BEST MODE

Figure 1:
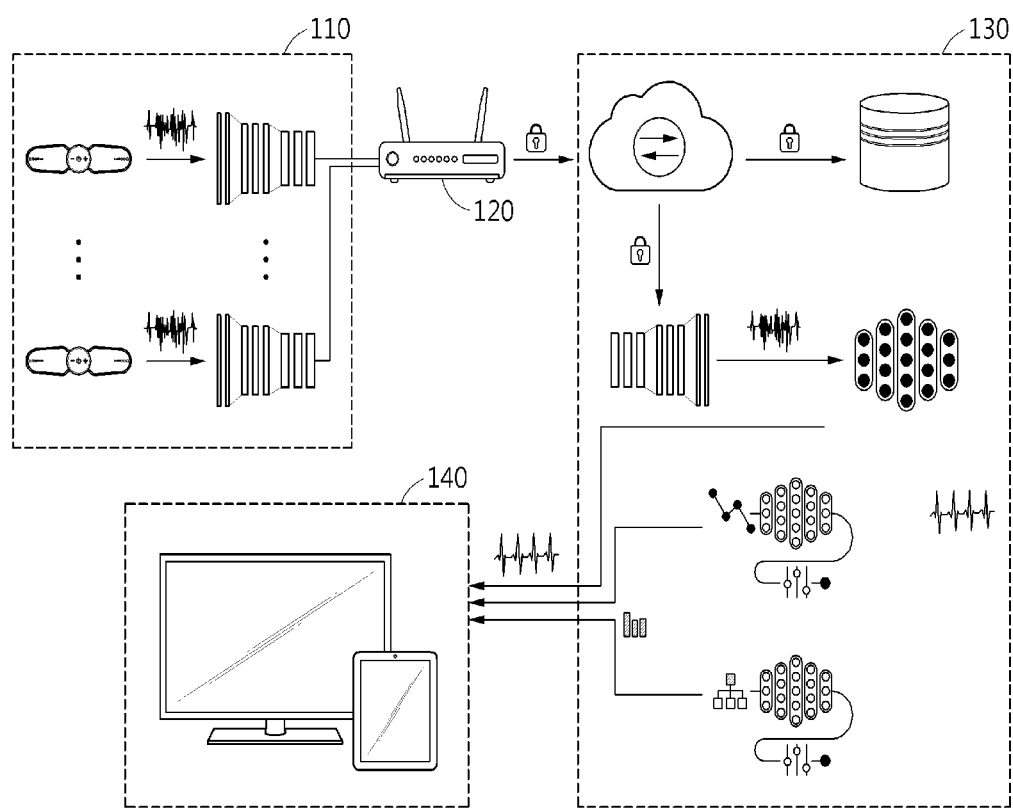
FIG. 1 is a diagram for explaining a heart condition monitoring system according to one embodiment of the present invention.

Hereinafter, preferred embodiments of the present invention will be described in detail with reference to the accompanying drawings.

However, it should be understood that the present invention is not limited to the embodiments according to the concept of the present invention, but includes changes, equivalents, or alternatives falling within the spirit and scope of the present invention.

In the following description of the present invention, detailed description of known functions and configurations incorporated herein will be omitted when it may make the subject matter of the present invention unclear.

In addition, the terms used in the specification are defined in consideration of functions used in the present invention, and can be changed according to the intent or conventionally used methods of clients, operators, and users. Accordingly, definitions of the terms should be understood on the basis of the entire description of the present specification.

In description of the drawings, like reference numerals may be used for similar elements. The singular expressions in the present specification may encompass plural expressions unless clearly specified otherwise in context.

In this specification, expressions such as "A or B" and "at least one of A and/or B" may include all possible combinations of the items listed together.

Expressions such as "first" and "second" may be used to qualify the elements irrespective of order or importance, and are used to distinguish one element from another and do not limit the elements.

It will be understood that when an element (e.g., first) is referred to as being "connected to" or "coupled to" another element (e.g., second), it may be directly connected or coupled to the other element or an intervening element (e.g., third) may be present.

As used herein, "configured to" may be used interchangeably with, for example, "suitable for", "ability to", "changed to", "made to", "capable of", or "designed to" in terms of hardware or software.

In some situations, the expression "device configured to" may mean that the device "may do~" with other devices or components.

For example, in the sentence "processor configured to perform A, B, and C", the processor may refer to a general purpose processor (e.g., CPU or application processor) capable of performing corresponding operation by running a dedicated processor (e.g., embedded processor) for performing the corresponding operation, or one or more software programs stored in a memory device.

In addition, the expression "or" means "inclusive or" rather than "exclusive or".

That is, unless mentioned otherwise or clearly inferred from context, the expression "x uses a or b" means any one of natural inclusive permutations.

Terms, such as "unit" or "module", etc., should be understood as a unit that processes at least one function or operation and that may be embodied in a hardware manner, a software manner, or a combination of the hardware manner and the software manner.

FIG. 1 is a diagram for explaining a heart condition monitoring system according to one embodiment of the present invention.

Referring to FIG. 1, a heart condition monitoring system 100 may include a sensor device 110 for detecting a heart condition, a gateway 120, a server 130, and a user terminal 140.

According to one embodiment of the present invention, the sensor device 110 for detecting a heart condition measures biosignals including at least one of an electrocardiogram signal, a motion signal, and a body temperature signal from a user. The measured biosignals are compressed and encoded using an artificial intelligence encoder, and the biosignals are transmitted to the gateway 120 using a low-power Bluetooth.

For example, the artificial intelligence encoder may divide and normalize biosignals into signals having the same length through sliding window technology as a pre-processing process for applying measured biosignals to a deep learning model.

For example, the length of a window may be 2 seconds, and an update period may be 1 second.

Here, a signal having a relatively short measurement time may also be analyzed through sliding window. Through the normalization process, various signal amplitudes and offsets may be set so that a deep learning model does not influence. In addition, the configuration of the artificial intelligence encoder will be described with reference to FIG. 3.

The gateway 120 transmits a transmitted signal to the server 130.

The gateway 120 is linked to the sensor device 110 for detecting a heart condition and the server 130, supports setting of environments such as hospitals, wards, and bed numbers and data collection and storage for each patient performed by the server 130, and supports battery low event transmission, process monitoring, and automatic fail over.

In addition, the gateway 120 supports automatic node searching, registration, and connection of the sensor device 110 for detecting a heart condition, and supports checking the remaining battery level of a low-power Bluetooth communication interface and the sensor device 110 for detecting a heart condition.

The server 130 may extract biosignals measured by the sensor device 110 for detecting a heart condition using an artificial intelligence decoder. The server 130 may perform machine learning and analysis of electrocardiogram signals of the extracted biosignals using a pre-stored artificial intelligence algorithm to optimize detection performance of a heart condition using public biosignal data sets measured in various environments, or may perform model learning and performance evaluation on biosignals measured by the sensor device 110 for detecting a heart condition by using the structure of biosignal artifact removal artificial intelligence developed for multimodal biosignals.

In addition, to reflect various patterns of electrocardiogram signals in a risk assessment model based on an artificial intelligence algorithm, the server 130 uses feature information extracted from the time domain of the electrocardiogram signals.

For example, the server 130 may use machine learning models such as a convolutional neural network (CNN) and a deep belief network (DBN) or various machine learning techniques such as Gradient Boost and XGBooST to determine a classification model for classifying major cardiovascular diseases such as myocardial infarction and coronary artery disease.

In addition, the server 130 may evaluate the effectiveness of a classification model by calculating the accuracy of the classification model through result comparison using a machine learning technique such as support vector machine (SVM) and random forest (RF) based on a public biosignal dataset.

In addition, the server 130 may determine a cardiovascular disease related to a user's heart condition learned and analyzed using an artificial intelligence algorithm, and may transmit the determined cardiovascular disease and the analysis result to a user terminal 140 to assist medical staff in diagnosing a cardiovascular disease or to easily recognize change in a patient's prognosis.

Accordingly, the present invention may determine a classification model for major cardiovascular diseases such as myocardial infarction and coronary artery diseases based on a sensor device for detecting a heart condition that is attached to a patient and detects the heart condition of the patient, biosignals related to a heart condition, and a server using artificial intelligence algorithm and prevent misdiagnosis by doctors and occurrence of false alarms based on the determined major cardiovascular disease classification model.

In addition, the present invention may provide a heart condition monitoring system based on IoT and artificial intelligence for elderly patient management through real-time monitoring of patient's multimodal biosignals measured by a sensor device for detecting a heart condition that is attached to a patient and detects the heart condition of the patient.

Figure 2:
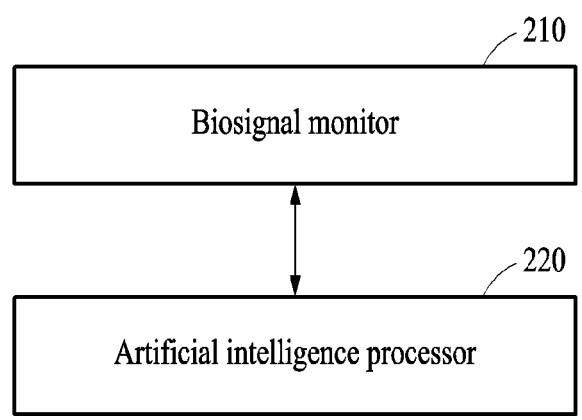
FIG. 2 is a diagram for explaining the components of a sensor device for detecting a heart condition according to one embodiment of the present invention.

FIG. 2 is a diagram for explaining the components of a sensor device for detecting a heart condition according to one embodiment of the present invention.

Referring to FIG. 2, a sensor device 200 for detecting a heart condition includes a biosignal monitor 210 and an artificial intelligence processor 220.

According to one embodiment of the present invention, the sensor device 200 for detecting a heart condition is attached to the upper part of or near the heart of a user to measure heart condition-related data from the user, or is worn as a wearable device in the form of a band on the user's wrist to measure heart condition-related data.

For example, the biosignal monitor 210 may measure biosignals including an electrocardiogram signal, a motion signal, and a body temperature signal from a user, and may output monitoring information including the measured biosignals through an artificial intelligence encoder.

According to one embodiment of the present invention, the biosignal monitor 210 may encode and compress at least one of heart condition information according to change in a user's heart condition, movement state information according to change in user's movement, and body temperature information through an artificial intelligence encoder and output the information.

For example, the artificial intelligence processor 220 may extract electrocardiogram signals included in output monitoring information.

In addition, the artificial intelligence processor 220 may extract morphological information as feature information by converting the extracted electrocardiogram signals into a time-standardized image based on a pre-stored artificial intelligence machine learning algorithm. In addition, the artificial intelligence processor 220 may determine a plurality of cardiac abnormality type models using the extracted feature information, calculate classification accuracy for the determined cardiac abnormality type models, and determine a cardiovascular disease of a user using the determined cardiac abnormality type models and public cardiovascular disease data based on the calculated accuracy.

For example, the artificial intelligence processor 220 may automatically calculate the classification accuracy by comparing an open data set and cardiac abnormality type models based on an artificial intelligence learning technique.

According to one embodiment of the present invention, the artificial intelligence processor 220 may simulate data traffic generated when electrocardiogram signals are measured, and may determine the operating state of the sensor device for detecting a heart condition based on the simulation.

For example, the artificial intelligence processor 220 may periodically check a battery state, determine a low battery state, and provide alarm information.

For example, the artificial intelligence processor 220 may include a convolutional neural network layer and a bidirectional long short-term memory (BLSTM) layer.

According to one embodiment of the present invention, the artificial intelligence processor 220 may transmit monitoring information to a server to detect emergency states including cardiac arrest and a fall of a user based on a least one of an electrocardiogram signal and a motion signal.

Accordingly, the present invention may provide a sensor device for detecting a heart condition that detects the heart condition of a patient for heart condition analysis for real-time arrhythmia detection, biosignal quality management to improve signal analysis reliability, and assessment of major cardiovascular diseases for early disease management.

In addition, the present invention may detect major cardiac abnormalities such as tachycardia, bradycardia, atrial fibrillation, left bundle branch block (LBBB), right bundle branch block (RBBB), premature atrial contraction (PAC), premature ventricular contraction (PVC), and cardiac arrest by analyzing, based on a pre-stored artificial intelligence algorithm, biosignals measured by a sensor device for detecting a heart condition that is attached to a patient and detects the heart condition of the patient.

That is, the sensor device 200 for detecting a heart condition according to one embodiment of the present invention may transmit monitoring information for classifying left bundle branch block, right bundle branch block, premature atrial contraction, and premature ventricular contraction related to arrhythmia to the server.

In addition, the sensor device 200 for detecting a heart condition according to one embodiment of the present invention may perform machine learning of monitoring information to classify left bundle branch block, right bundle branch block, premature atrial contraction, and premature ventricular contraction related to arrhythmia, and may provide the classified information.

Figure 3:
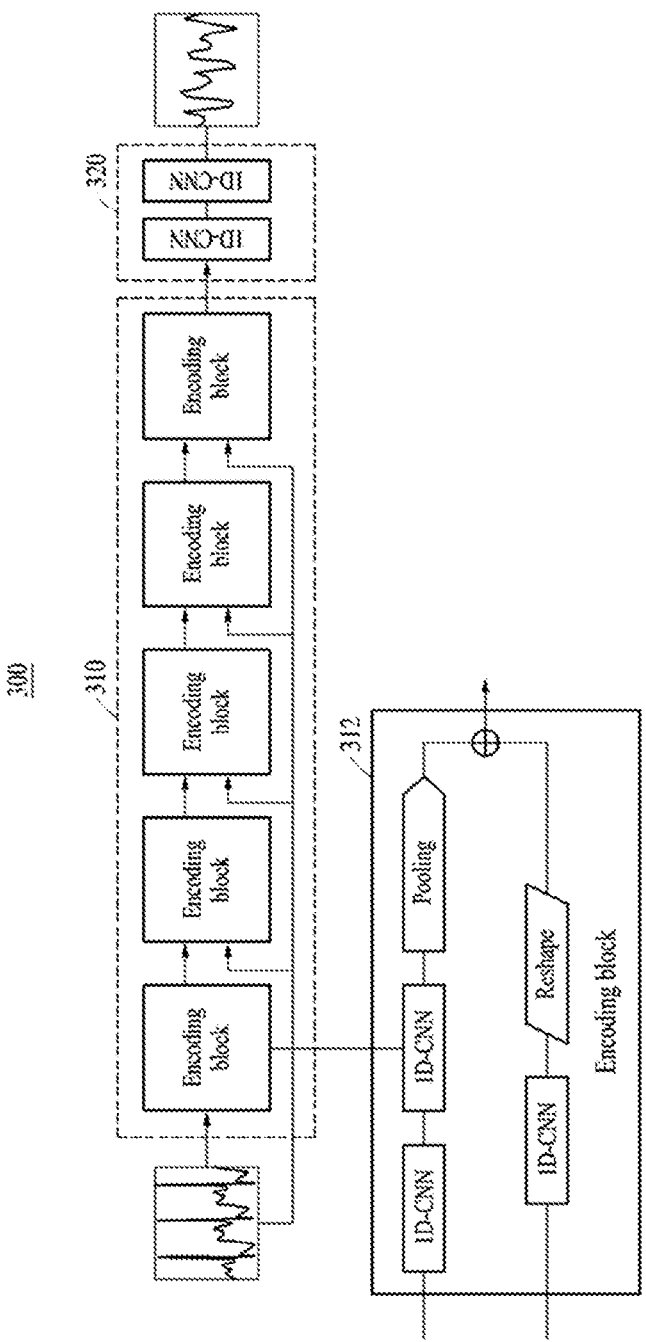
FIG. 3 is a diagram for explaining a deep learning model related to the artificial intelligence encoder of a sensor device for detecting a heart condition according to one embodiment of the present invention.

FIG. 3 is a diagram for explaining a deep learning model related to the artificial intelligence encoder of a sensor device for detecting a heart condition according to one embodiment of the present invention.

Referring to FIG. 3, an artificial intelligence encoder 300 may include an encoding block 310 and a deep learning neural network 320, and the encoding block 310 may include a deep learning neural network layer, a pooling layer, and a reshape layer.

The artificial intelligence encoder 300 according to one embodiment of the present invention may compress a signal for morphological information through conversion of electrocardiogram signals into a time-standardized image, and may output the compressed signal as monitoring information.

For example, the artificial intelligence encoder 300 may include a convolutional neural network layer and a bidirectional long short-term memory layer.

For example, the artificial intelligence encoder 300 may transmit approximately 64 times compressed signal information to the artificial intelligence processor of the sensor device for detecting a heart condition or the artificial intelligence processor of the server.

For example, morphological information through conversion into a time-standardized image may be generated based on signals divided and normalized into signals having the same length through a sliding window technique.

Figure 4A:
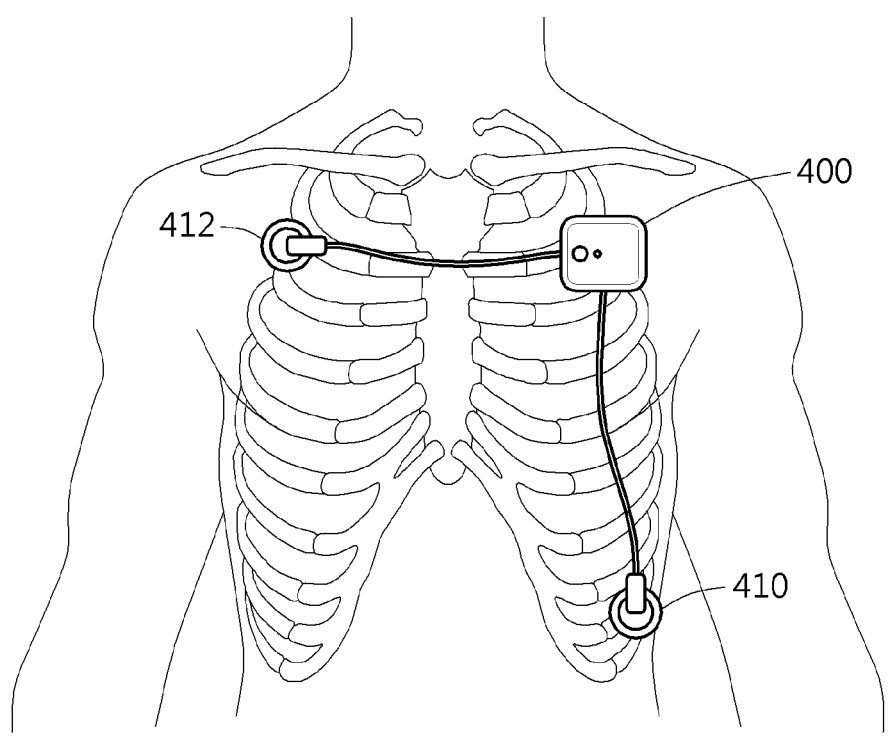
FIGS. 4A and 4B are diagrams for explaining a sensor device for detecting a heart condition according to one embodiment of the present invention.
Figure 4B:
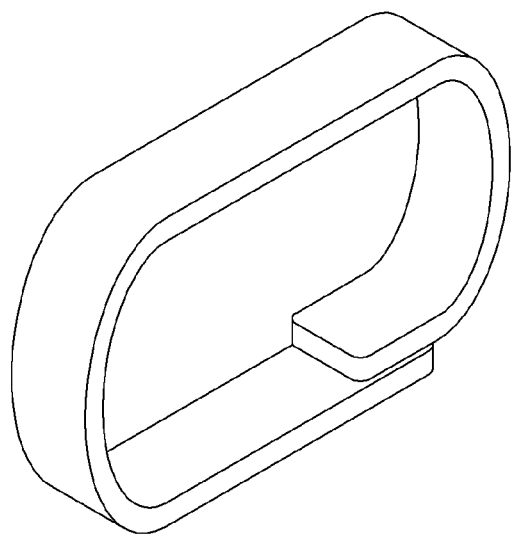

FIGS. 4A and 4B are diagrams for explaining a sensor device for detecting a heart condition according to one embodiment of the present invention.

FIG. 4A illustrates a case in which a sensor device 400 for detecting a heart condition according to one embodiment of the present invention includes three leads, the leads are connected to each other, and the three leads are worn by a user.

Referring to FIG. 4A, the sensor device 400 for detecting a heart condition is configured by connecting three leads. A first lead is positioned at the sensor device 400 for detecting a heart condition, and a second lead 410 and a third lead 412 made of an adhesive material are attached to two parts of the user's body.

For example, the sensor device 400 for detecting a heart condition may be a main body of a sensor device for detecting a heart condition. The first lead may be positioned at one measurement point, and information measured through the second lead 410 and the third lead 412 may be integrated to measure a biosignal.

According to one embodiment of the present invention, the sensor device 400 for detecting a heart condition may include a power supply, a sensor, and a first lead, and the sensor may measure electrocardiogram (ECG), physical activity measurement (Actigraph), and a body temperature.

For example, the second lead 410 and the third lead 412 may be connected to the sensor device 400 for detecting a heart condition through covered wire.

For example, the sensor device 400 for detecting a heart condition may monitor a heart condition by electrocardiogram (ECG) measured as a biosignal, and may compress and encode electrocardiogram signals according to the heart condition through an artificial intelligence encoder and output the electrocardiogram signals.

For example, the sensor device 400 for detecting a heart condition may monitor a body reaction by physical activity measurement measured as a biosignal, and may compress and encode motion signals according to the body reaction through an artificial intelligence encoder and output the motion signals.

For example, the sensor device 400 for detecting a heart condition may compress and encode a body temperature signal measured as a biosignal through an artificial intelligence encoder and output the body temperature signal.

FIG. 4B illustrates a case in which a sensor device 420 for detecting a heart condition according to one embodiment of the present invention consists of one lead and is worn by a user.

Referring to FIG. 4B, the sensor device 420 for detecting a heart condition may be a wearable device in the form of a wristband.

According to one embodiment of the present invention, the sensor device 420 for detecting a heart condition may include a power supply, a sensor, and a lead, and the sensor may measure electrocardiogram (ECG), physical activity measurement (Actigraph) and a body temperature.

For example, the sensor device 420 for detecting a heart condition may monitor a heart condition by electrocardiogram (ECG) measured as a biosignal, and may compress and encode electrocardiogram signals according to the heart condition through an artificial intelligence encoder and output the electrocardiogram signals.

For example, the sensor device 420 for detecting a heart condition may monitor a body reaction by physical activity measurement measured as a biosignal, and may compress and encode motion signals according to the body reaction through an artificial intelligence encoder and output the motion signals.

For example, the sensor device 420 for detecting a heart condition may compress and encode a body temperature signal measured as a biosignal through an artificial intelligence encoder and output the body temperature signal.

According to one embodiment of the present invention, the sensor device 400 for detecting a heart condition and the sensor device 420 for detecting a heart condition may provide measured electrocardiogram signals as data applicable to a heart condition analysis technique for real-time arrhythmia detection, a biosignal quality management artificial intelligence technique for improving signal analysis reliability, and a major cardiovascular disease assessment artificial intelligence technique for early disease management.

For example, the sensor device 400 for detecting a heart condition may perform cardiac function monitoring more accurately than the sensor device 420 for detecting a heart condition. On the other hand, from the viewpoint of convenience in the user's daily life, the sensor device 420 for detecting a heart condition is better than the sensor device 400 for detecting a heart condition.

FIG. 5 is a diagram for explaining the additional components of a sensor device for detecting a heart condition according to one embodiment of the present invention.

Referring to FIG. 5, a sensor device 500 for detecting a heart condition includes a micro USB port 510, a lithium polymer battery 520, a power/action switch 530, an ECG sensor 540, an acceleration/angular velocity sensor 550, and a low-power Bluetooth/Wi-Fi 560, and controls the above-described components through a microcontroller 570.

According to one embodiment of the present invention, the sensor device 500 for detecting a heart condition may charge the lithium polymer battery 520 using the micro USB port 510.

For example, the power/action switch 530 may operate the sensor device 500 for detecting a heart condition when receiving a user's push input.

For example, the ECG sensor 540 measures the electrocardiogram signals of a user, and the acceleration/angular velocity sensor 550 measures the motion signals of a user.

According to one embodiment of the present invention, the sensor device 500 for detecting a heart condition may control the low-power Bluetooth/Wi-Fi 560 to be linked to a gateway located in a hospital room or home, and may transmit at least one of an electrocardiogram signal and a motion signal measured by the ECG sensor 540 and the acceleration/angular velocity sensor 550 to the server through the gateway.

FIG. 6 is a diagram for explaining the flow of major events of biosignal measurement and data transmission according to one embodiment of the present invention.

Referring to FIG. 6, the biosignal monitor may measure high resolution/speed ECG through an ECG sensor 610. In addition, the biosignal monitor may perform A/D conversion of ECG sampled at 100 Hz having a resolution of 14 bit or more through an AD converter 620.

In addition, a microcontroller 630 is responsible for overall control of each component and signal processing, and a low-power Bluetooth/Wi-Fi module 640 provides a short-range wireless communication function or enables wired/wireless data communication by accessing a network. In particular, in the present invention, data may be transmitted to ECG and a 6-Axis MEMS sensor by using the low-power Bluetooth/Wi-Fi module 640.

In addition, at reference numeral 650, a function of a battery state measuring module for measuring a state of a battery for a device is performed. Reference numeral 660 is a 3-axis accelerometer, and reference numeral 670 is 3-axis gyroscope MEMS motion tracking.

The 3-axis accelerometer and the 3-axis gyroscope MEMS motion tracking may measure the minimum ±16 g range, 16 bit 100 Hz angular velocity, and may measure the maximum ±2,000 dps range, 16 bit 100 Hz angular velocity.

Figure 7:
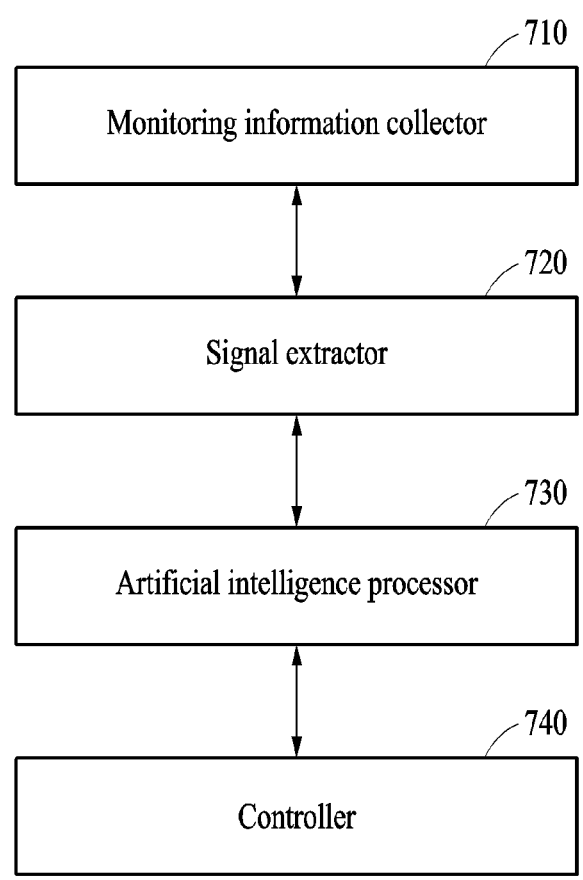
FIG. 7 is a diagram for explaining the components of a server according to one embodiment of the present invention.

FIG. 7 is a diagram for explaining the components of a server according to one embodiment of the present invention.

Referring to FIG. 7, a server 700 includes a monitoring information collector 710, a signal extractor 720, an artificial intelligence processor 730, and a controller 740.

According to one embodiment of the present invention, the server 700 may be linked to the sensor device for detecting a heart condition to provide user condition information.

For example, the monitoring information collector 710 may collect monitoring information including biosignals including electrocardiogram signals measured from a user.

For example, the monitoring information collector 710 may collect monitoring information transmitted through a gateway by the sensor device for detecting a heart condition.

For example, the biosignal may be interpreted as a signal measured through an electrode when the sensor device for detecting a heart condition is attached to the user's heart.

According to one embodiment of the present invention, the signal extractor 720 may extract electrocardiogram signals for analyzing a user's heart condition from transmitted monitoring information using an artificial intelligence algorithm.

For example, the signal extractor 720 may decode the collected monitoring information to extract biosignals corresponding to electrocardiogram signals from the monitoring information.

In addition, the signal extractor 720 may convert, using an artificial intelligence decoder, biosignals encoded and compressed by the artificial intelligence encoder of the sensor device for detecting a heart condition into biosignals.

According to one embodiment of the present invention, the artificial intelligence processor 730 may extract morphological information as feature information by converting extracted electrocardiogram signals into a time-standardized image based on a pre-stored artificial intelligence machine learning algorithm, may determine a plurality of cardiac abnormality type models using the extracted feature information, may calculate classification accuracy for the determined cardiac abnormality type models, and may determine a cardiovascular disease of a user using the determined cardiac abnormality type models and public cardiovascular disease data based on the calculated accuracy.

Specifically, the artificial intelligence processor 730 may generate normalized signals based on the time domain of electrocardiogram signals, may convert the generated normalized signals into a time-standardized image, may generate compressed signals by applying a pre-stored artificial intelligence machine learning algorithm-based weight to the converted image, may generate reconstructed signals from compressed signals using the applied weight, and may extract feature information corresponding to morphological features of the electrocardiogram signals by performing machine learning of the weight so that a difference between the generated normalized signals and the generated reconstructed signals falls within a preset threshold range.

For example, the artificial intelligence processor 730 may include a convolutional neural network layer and a bidirectional long short-term memory (BLSTM) layer.

In addition, the artificial intelligence processor 730 may perform machine learning of feature information to determine a plurality of cardiac abnormality type models as at least one model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

For example, the artificial intelligence processor 730 may calculate classification accuracy for the determined cardiac abnormality type models.

Specifically, the artificial intelligence processor 730 may calculate classification accuracy for a plurality of cardiac abnormality type models based on Equation 1 below.

$$\text{Accuracy}=(TP+TN)/(TP+TN+FP+FN) \quad \text{[Equation 1]}$$

In Equation 1, TP may represent a case in which an abnormal state is accurately classified as an abnormal state, TN may represent a case in which a normal state is classified as a normal state, FP may represent a case in which a normal state is classified as an abnormal state, and FN may represent a case in which a normal state is classified as an abnormal state.

According to one embodiment of the present invention, the artificial intelligence processor 730 uses an open data set, at least one of a tachycardia model, a bradycardia model, an atrial fibrillation model, a left bundle branch block model, a right bundle branch block model, a premature atrial contraction model, and a premature ventricular contraction model, and a normal heart condition model to classify a true positive (TP) case in which cardiac abnormality is classified as cardiac abnormality, a false negative (FN) case in which cardiac abnormality is classified as normal, a false positive (FP) case in which normal is classified as cardiac abnormality, and a true negative (TN) case in which normal is classified as normal.

Next, the artificial intelligence processor 730 may calculate classification accuracy for at least one of a tachycardia model, a bradycardia model, an atrial fibrillation model, a left bundle branch block model, a right bundle branch block model, a premature atrial contraction model, and a premature ventricular contraction model based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

For example, the artificial intelligence processor 730 may automatically calculate the classification accuracy by comparing an open data set and cardiac abnormality type models based on an artificial intelligence learning technique.

In addition, the artificial intelligence processor 730 may use an open data set, a cardiac arrest model, and a normal heart condition model to classify a true positive (TP) case in which a cardiac arrest section is classified as a cardiac arrest section, a false negative (FN) case in which a cardiac arrest section is classified as a normal section, a false positive (FP) case in which a normal section is classified as a cardiac arrest section, and a true negative (TN) case in which a normal section is classified as a normal section.

Next, the artificial intelligence processor 730 may calculate classification accuracy for emergency states based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

In addition, the artificial intelligence processor 730 may classify a true positive (TP) case in which an artifact signal is classified as an artifact signal, a false negative (FN) case in which an artifact signal is classified as a normal signal, a false positive (FP) case in which a normal signal is classified as an artifact signal, and a true negative (TN) case in which a normal signal is classified as a normal signal, and may calculate artifact removal accuracy based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

According to one embodiment of the present invention, the artificial intelligence processor 730 may include signal quality management artificial intelligence, arrhythmia detection artificial intelligence, and cardiovascular disease evaluation artificial intelligence. In addition, the artificial intelligence processor 730 may manage the signal quality of biosignals transmitted from the sensor device for detecting a heart condition, and may evaluate and detect arrhythmias and cardiovascular diseases.

According to one embodiment of the present invention, the controller 740 may control to provide a cardiovascular disease determined by the artificial intelligence processor 730 to a user terminal. Here, the controlled device may be a communication device.

For example, the user terminal may receive analysis information related to cardiovascular diseases, and may provide cardiovascular disease determination information and analysis results included in the received analysis information through a display.

According to one embodiment of the present invention, after at least one of an electrocardiogram signal and a motion signal is measured, the controller 740 may calculate the number of measured electrocardiogram signals or the number of measured motion signals, and may compare the calculated number of electrocardiogram signals or the calculated number of motion signals with a threshold value to confirm the data reception state of the electrocardiogram signals or the motion signals.

In addition, when the reception state of the electrocardiogram signals or the motion signals is poor, the controller 740 may request additional data or additional measurement from the sensor device for detecting a heart condition.

Accordingly, the present invention may contribute to diagnosis assistance and reduction of medical costs through continuous monitoring of arrhythmias.

In addition, the present invention may reduce the number of false alarms occurring in a ward by accurately measuring and analyzing the current condition of a patient, and thus may improve the work efficiency of medical staff and the prognosis of a patient.

In addition, the present invention may provide a function for evaluating the risk of chronic diseases through analysis of pulse waves and electrocardiogram waveforms using an artificial intelligence learning technique.

Figure 8:
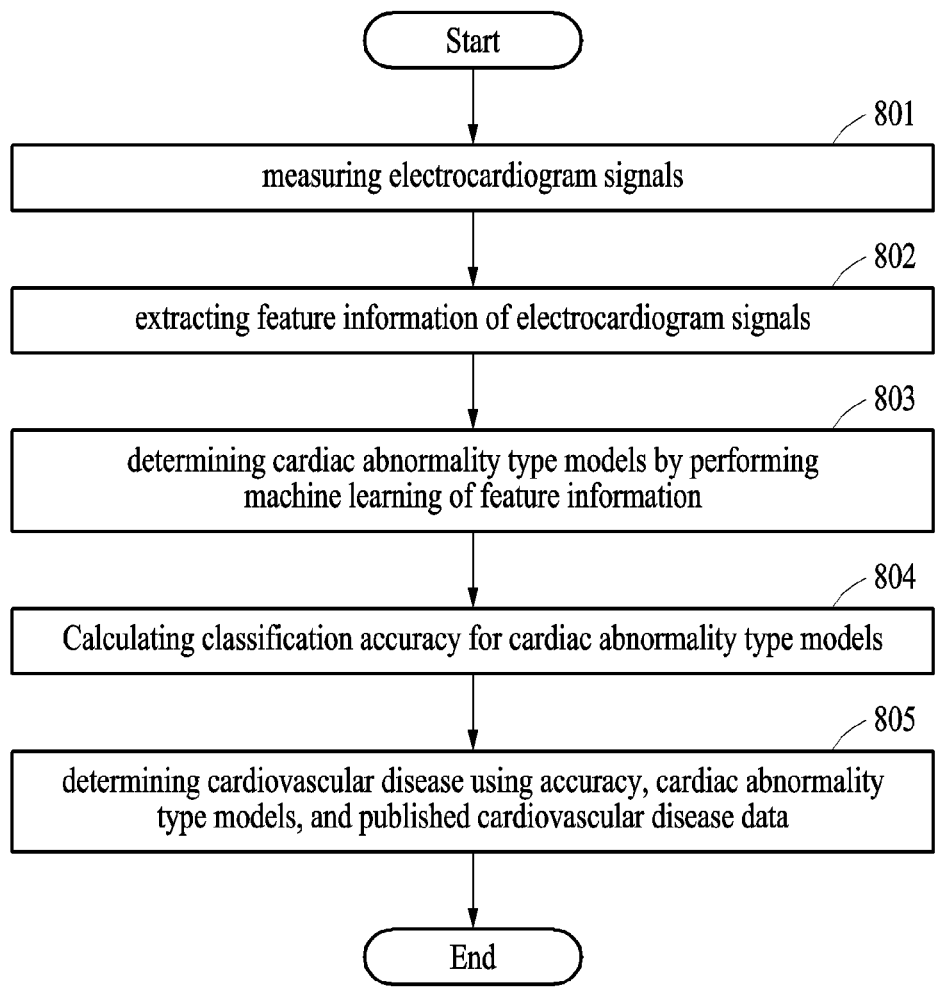
FIGS. 8 and 9 are flowcharts for explaining a method of monitoring a heart condition according to one embodiment of the present invention.
Figure 9:
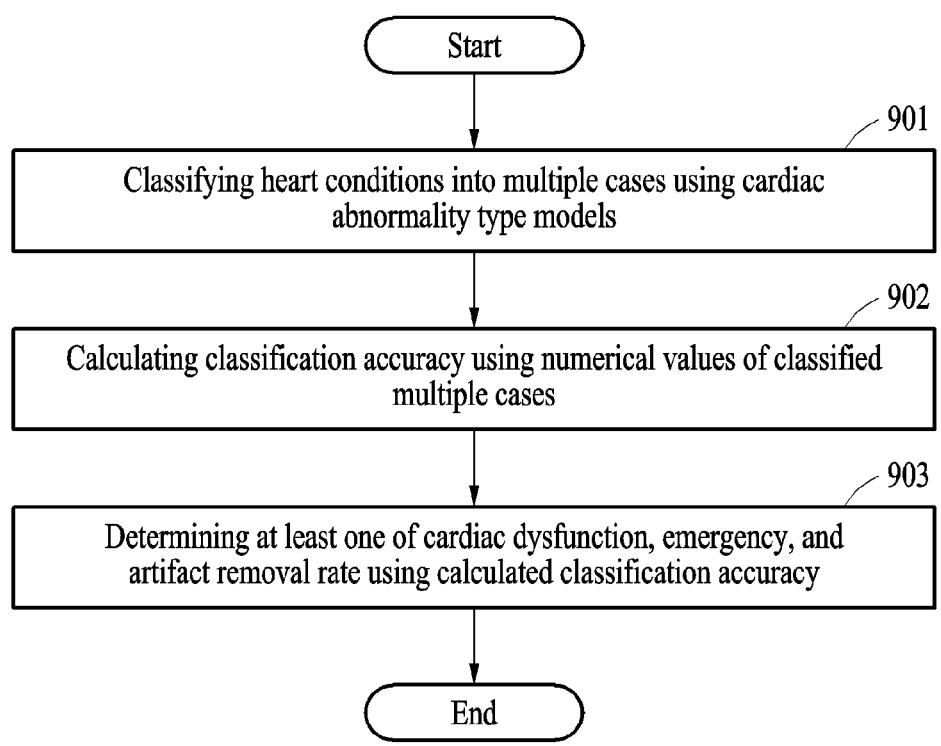

FIGS. 8 and 9 are flowcharts for explaining a method of monitoring a heart condition according to one embodiment of the present invention.

FIG. 8 illustrates an embodiment that assists in determining a cardiovascular disease of a user after learning and analyzing, using a pre-stored artificial intelligence algorithm, biosignals measured using a sensor device for detecting a heart condition according to the method of monitoring a heart condition according to one embodiment of the present invention.

Referring to FIG. 8, in the method of monitoring a heart condition according to one embodiment of the present invention, in step 801, electrocardiogram signals are measured.

That is, according to the method of monitoring a heart condition, electrocardiogram signals are measured using the sensor device for detecting a heart condition attached to a user.

According to the method of monitoring a heart condition according to one embodiment of the present invention, in step 802, the feature information of electrocardiogram signals is extracted.

That is, according to the method of monitoring a heart condition, machine learning of the time domain of electrocardiogram signals is performed to extract feature information.

Specifically, according to the method of monitoring a heart condition, normalized signals generated based on the time domain of electrocardiogram signals may be converted into a time-standardized image, a pre-stored artificial intelligence machine learning algorithm-based weight may be applied to the converted image to generate a compressed signal, a reconstructed signal may be generated from the compressed signal using the applied weight, and feature information corresponding to the morphological feature of the electrocardiogram signals may be extracted by performing machine learning of the weight so that a difference between the generated normalized signal and the generated reconstructed signal falls within a preset threshold range.

According to the method of monitoring a heart condition according to one embodiment of the present invention, in step 803, cardiac abnormality type models are determined by performing machine learning of the feature information.

That is, according to the method of monitoring a heart condition, in step 802, the extracted feature information may be machine-learned to determine a plurality of cardiac abnormality type models as at least one model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

According to the method of monitoring a heart condition according to one embodiment of the present invention, in step 804, classification accuracy for a plurality of cardiac abnormality type models is calculated.

That is, according to the method of monitoring a heart condition, depending on the determination result of a plurality of cardiac abnormality type models, classification accuracy for the cardiac abnormality type models may be quantified.

In the method of monitoring a heart condition, the step of calculating classification accuracy for a plurality of cardiac abnormality type models will be further described with reference to FIG. 9.

According to the method of monitoring a heart condition according to one embodiment of the present invention, in step 805, a cardiovascular disease is determined using the accuracy, the cardiac abnormality type models, and public cardiovascular disease data.

That is, according to the method of monitoring a heart condition, based on the accuracy calculated in step 804, the cardiac abnormality type models determined in step 803 are compared with public cardiovascular disease data as public data to determine a cardiovascular disease of a user wearing the sensor device for detecting a heart condition.

According to the method of monitoring a heart condition according to one embodiment, in step 801, motion signals and a body temperature signal may be further measured from a user.

Thus, according to the method of monitoring a heart condition, monitoring information further including motion signals may be output through an artificial intelligence encoder, and emergency states including cardiac arrest and a fall of a user may be detected based on the measured electrocardiogram signals and the measured motion signals.

FIG. 9 illustrates an embodiment of performing evaluation of a plurality of cardiac abnormality type models determined by learning and analyzing, using a pre-stored artificial intelligence algorithm, biosignals measured using the sensor device for detecting a heart condition according to the method of monitoring a heart condition according to one embodiment of the present invention.

Referring to FIG. 9, according to the method of monitoring a heart condition according to one embodiment of the present invention, in step 901, the heart condition is divided into a plurality of cases using cardiac abnormality type models.

That is, according to the method of monitoring a heart condition, each of a plurality of cardiac abnormality type models may be classified into four cases including a true positive (TP) case in which cardiac abnormality is classified as cardiac abnormality, a false negative (FN) case in which cardiac abnormality is classified as normal, a false positive (FP) case in which normal is classified as cardiac abnormality, and a true negative (TN) case in which normal is classified as normal.

According to the method of monitoring a heart condition according to one embodiment of the present invention, in step 902, classification accuracy is calculated using the numerical values of the cases classified in step 901.

That is, in the method of monitoring a heart condition, classification accuracy is calculated based on a ratio of a combination of a numerical value of the true positive (TP)

case and a numerical value of the true negative (TN) case to a combination of a numerical value of the true positive (TP) case, a numerical value of the false negative (FN) case, a numerical value of the false positive (FP) case, and a numerical value of the true negative (TN) case.

According to the method of monitoring a heart condition according to one embodiment of the present invention, in step 903, at least one of cardiac dysfunction, an emergency state, and an artifact removal rate may be determined using the classification accuracy calculated in step 902.

That is, according to the method of monitoring a heart condition, when classification accuracy of cardiac abnormality types related to tachycardia, bradycardia, atrial fibrillation, left bundle branch block, right bundle branch block, premature atrial contraction, and premature ventricular contraction with the numerical value of classification accuracy calculated in step 902 is higher than a threshold value, the type of cardiac abnormality may be determined as a least one of tachycardia, bradycardia, atrial fibrillation, left bundle branch block, right bundle branch block, premature atrial contraction, and premature ventricular contraction, an emergency state related to cardiac arrest may be determined, and an artifact removal rate may be determined based on artifact removal probability.

Accordingly, the present invention may detect major cardiac abnormalities such as tachycardia, bradycardia, atrial fibrillation, left bundle branch block, right bundle branch block, premature atrial contraction, premature ventricular contraction, and cardiac arrest by analyzing, based on a pre-stored artificial intelligence algorithm, biosignals measured by a sensor device for detecting a heart condition that is attached to a patient and detects the heart condition of the patient.

In addition, the present invention may improve the measurement accuracy of biosignals measured by a sensor device for detecting a heart condition that is attached to a patient and detects the heart condition of the patient by learning and evaluating the measurement accuracy of the biosignals by calculating cardiac dysfunction classification accuracy, emergency state classification accuracy, and artifact signal detection accuracy using a pre-stored artificial intelligence algorithm and an open data set.

Figure 10:
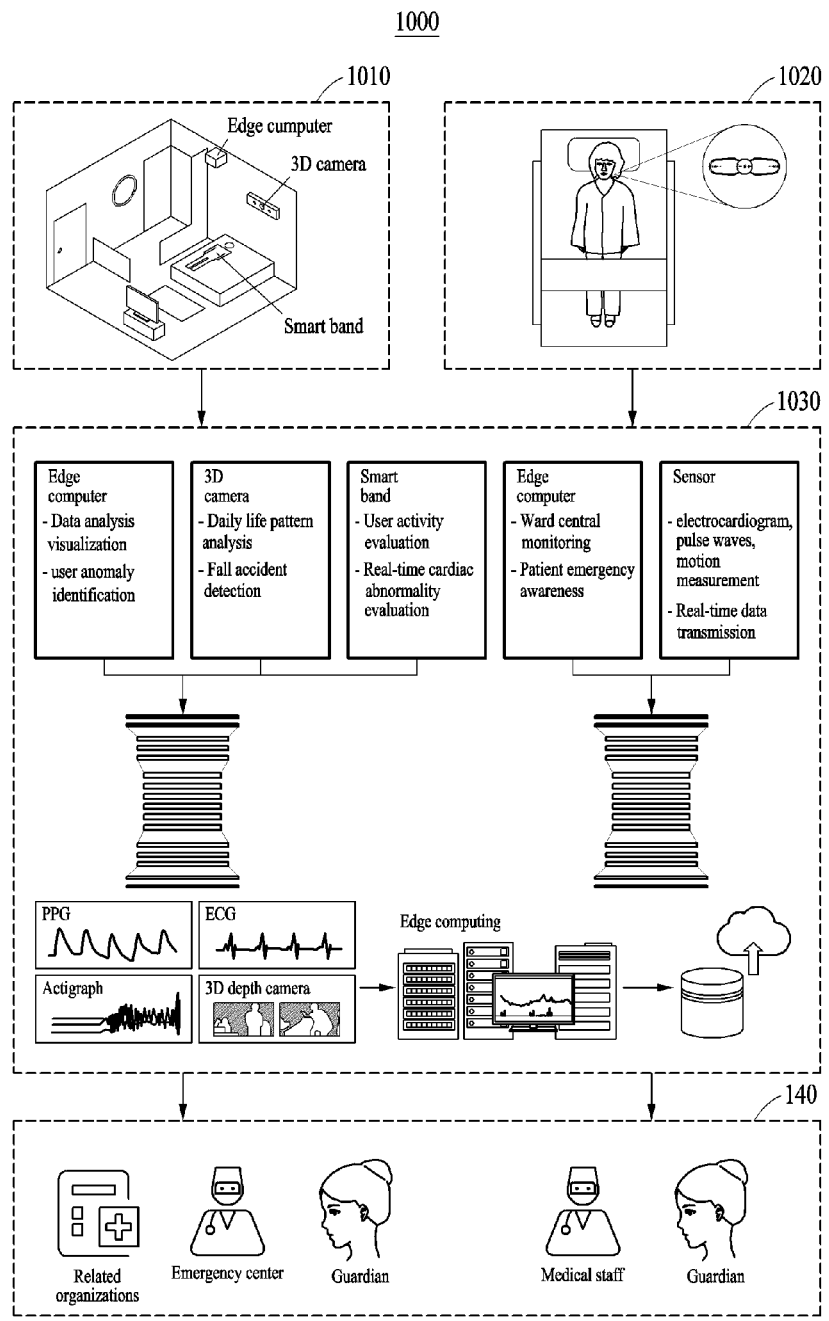
FIGS. 10 and 11 are diagrams for explaining a system for providing a life support complex solution according to one embodiment of the present invention.
Figure 11:
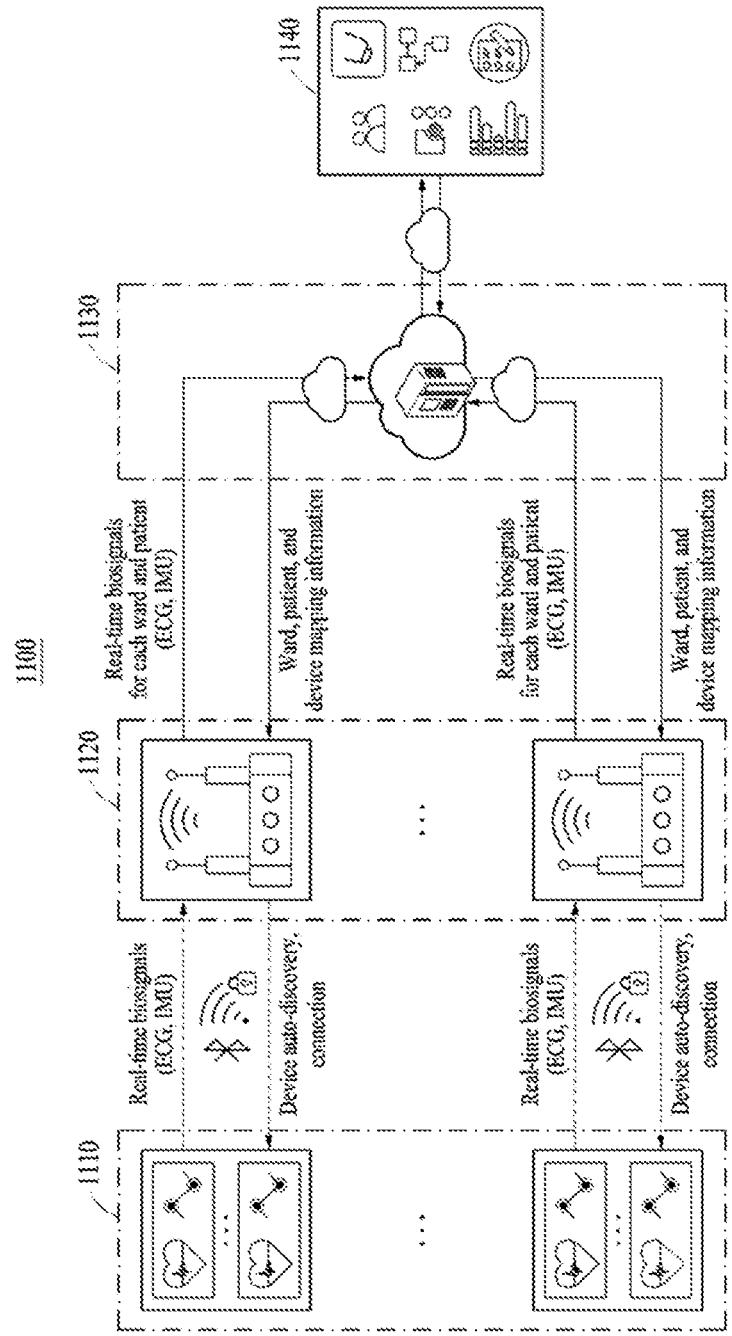

FIGS. 10 and 11 are diagrams for explaining a system for providing a life support complex solution according to one embodiment of the present invention.

FIG. 10 illustrates the components of the system for providing a life support complex solution according to one embodiment of the present invention.

Referring to FIG. 10, a system 1000 for providing a life support complex solution may provide a biosignal measurement device used in a living indoor monitoring system 1010 by combining the living indoor monitoring system 1010 and a heart condition monitoring system 1020 and a life support complex platform 1030 by combining the measurement data of the biosignal measurement device used in the heart condition monitoring system 1020.

According to one embodiment of the present invention, the life support complex platform 1030 may determine cardiac abnormality type models by performing analyzation and learning based on artificial intelligence, and may support more accurate determination of a cardiovascular disease based on evaluation of the determined cardiac abnormality type models, thereby providing a personalized medical service, and supporting heart disease-related decision-making.

Accordingly, the life support complex platform 1030 may determine cardiac abnormality type models by analyzing and learning measurement data of the biosignal measurement device based on artificial intelligence in a user terminal 1040 used by related institutions, emergency centers, guardians, and medical staff, and may support more accurate determination of a cardiovascular disease based on evaluation of the determined cardiac abnormality type models, thereby providing a personalized medical service, and supporting heart disease-related decision-making.

According to one embodiment of the present invention, the living indoor monitoring system 1010 may detect a fall accident of an applicant by acquiring a 3D image for analyzing the daily life pattern of the applicant through a 3D camera, and may provide a function of monitoring biosignals and real-time cardiac abnormality evaluation by using a smart band worn by an applicant.

According to one embodiment of the present invention, the heart condition monitoring system 1020 may monitor electrocardiograms, pulse waves, motions, and body temperatures of an applicant by using the heart condition detection sensor, transmit the data to a server in real time, and provide the transmitted data to a user terminal.

According to one embodiment of the present invention, the system 1000 for providing a life support complex solution may include a biosignal measurement device, a gateway, a server, and a user terminal.

For example, the biosignal measurement device may measure biosignals including at least one of an electrocardiogram signal, a motion signal, and a pulse wave signal from an applicant, and may transmit monitoring information including the measured biosignals.

In addition, the gateway may transmit the monitoring information to the server.

In addition, the server may extract electrocardiogram signals of the biosignals from the monitoring information transmitted from the biosignal measurement device, and may extract morphological information as feature information through conversion of the extracted electrocardiogram signals into a time-standardized image.

In addition, the server may determine a plurality of cardiac abnormality type models using the extracted feature information, may calculate classification accuracy for the determined cardiac abnormality type models, may determine a cardiovascular disease of the applicant and whether the applicant is in an emergency state using the determined cardiac abnormality type models and public cardiovascular disease data based on the calculated accuracy, and may feed-back information about the determined cardiovascular disease and whether the applicant is in an emergency state and change information of biosignals to a user terminal.

According to one embodiment of the present invention, the user terminal may include at least one of a medical staff terminal, a guardian terminal, and an emergency center terminal.

In addition, the user terminal may output information including at least one of information about the determined cardiovascular disease and whether an applicant is in an emergency state and change information of biosignals. Based on prescription information generated according to information output to a medical staff terminal, the prescription information may also be updated in a guardian terminal and an emergency center terminal.

For example, the applicant may correspond to at least one of an elderly person living alone, a disabled person, a serious patient, and a young patient.

Accordingly, the system 1000 for providing a life support complex solution may provide a life support complex solution to a facility for at least one of a ward for elderly persons living alone, a nursing hospital, and a silver town.

In addition, the system 1000 for providing a life support complex solution may help elderly health care, emergency detection, and prevention of sudden and lonely death, and may increase the efficiency of patient management based on monitoring in nursing hospitals and general wards.

Accordingly, the system 1000 for providing a life support complex solution may prevent sudden and lonely death of elderly persons living alone, may help manage heart condition in elderly persons living alone, may prevent chronic diseases of elderly persons living alone, and may provide rapid patient transfer and treatment in case of emergency.

Hereinafter, the components of the heart condition monitoring system 1020 will be further described with reference to FIG. 11.

FIG. 11 illustrates the components of a heart condition monitoring system in a system for providing a life support complex solution according to one embodiment of the present invention.

Referring to FIG. 11, a heart condition monitoring system 1100 may include a biosignal measurement device 1110, a gateway 1120, a server 1130, and a user terminal 1140.

According to one embodiment of the present invention, the biosignal measurement device 1110 measures biosignals including an electrocardiogram signal, a motion signal, and a body temperature signal from an applicant. The measured biosignals are compressed and encoded using an artificial intelligence encoder, and the biosignals are transmitted to the gateway 1120 using a low-power Bluetooth.

For example, the artificial intelligence encoder may divide and normalize biosignals into signals having the same length through sliding window technology as a pre-processing process for applying measured biosignals to a deep learning model.

For example, the length of a window may be 2 seconds, and an update period may be 1 second.

Here, a signal having a relatively short measurement time may also be analyzed through sliding window. Through the normalization process, various signal amplitudes and offsets may be set so that a deep learning model does not influence. In addition, the configuration of the artificial intelligence encoder will be described with reference to FIG. 4.

The gateway 1120 transmits transmitted signals to the server 1130.

The gateway 1120 is linked to a sensor device 1120 for detecting a heart condition and the server 1130, supports setting of environments such as hospitals, wards, and bed numbers and data collection and storage for each patient performed by the server 1130, and supports battery low event transmission, process monitoring, and automatic fail over.

In addition, the gateway 1120 supports automatic node searching, registration, and connection of the sensor device 1120 for detecting a heart condition, and supports checking the remaining battery level of a low-power Bluetooth communication interface and the sensor device 1120 for detecting a heart condition.

The server 1130 may extract biosignals measured by the sensor device 1120 for detecting a heart condition using an artificial intelligence decoder. The server 130 may perform machine learning and analysis of electrocardiogram signals of the extracted biosignals using a pre-stored artificial intelligence algorithm to optimize detection performance of a heart condition using public biosignal data sets measured in various environments, or may perform model learning and performance evaluation on biosignals measured by the sensor device 1120 for detecting a heart condition by using the structure of biosignal artifact removal artificial intelligence developed for multimodal biosignals.

In addition, to reflect various patterns of electrocardiogram signals in a risk assessment model based on an artificial intelligence algorithm, the server 1130 uses morphological information as feature information by converting the electrocardiogram signals into a time-standardized image.

For example, the server 1130 may use machine learning models such as a convolutional neural network (CNN) and a deep belief network (DBN) or various machine learning techniques such as Gradient Boost and XGBooST to determine a classification model for classifying major cardiovascular diseases such as myocardial infarction and coronary artery disease.

In addition, the server 1130 may evaluate the effectiveness of a classification model by calculating the accuracy of the classification model through result comparison using a machine learning technique such as support vector machine (SVM) and random forest (RF) based on a public biosignal dataset.

In addition, the server 1130 may determine a cardiovascular disease related to an applicant's heart condition learned and analyzed using an artificial intelligence algorithm, and may transmit the determined cardiovascular disease and the analysis result to the user terminal 1140 to assist medical staff in diagnosing a cardiovascular disease or to easily recognize change in a patient's prognosis.

Accordingly, the present invention may determine a classification model for major cardiovascular diseases such as myocardial infarction and coronary artery diseases based on a biosignal measurement device that is attached to a patient and detects the condition of the patient, biosignals related to a heart condition, and a server using artificial intelligence algorithm and prevent misdiagnosis by doctors and occurrence of false alarms based on the determined major cardiovascular disease classification model.

In addition, the present invention may provide a life support complex solution including a telemedicine service in preparation for the post-corona era.

Figure 12:
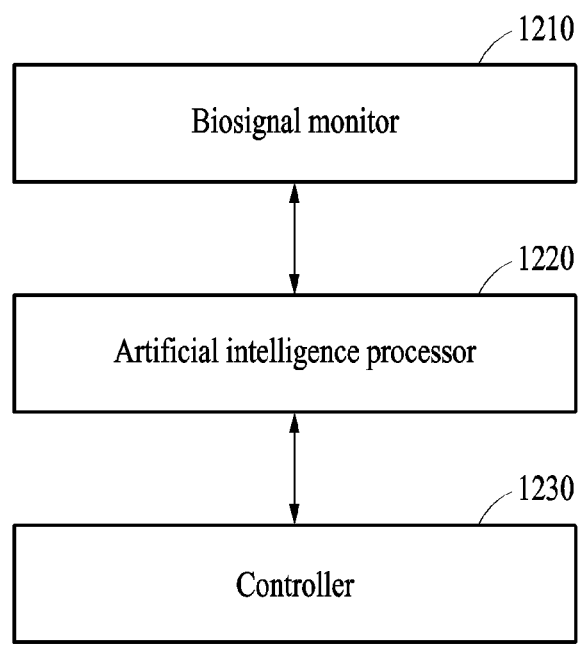
FIG. 12 is a diagram for explaining the components of a biosignal measurement device according to one embodiment of the present invention.

FIG. 12 is a diagram for explaining the components of a biosignal measurement device according to one embodiment of the present invention.

FIG. 12 illustrates the components of a biosignal measurement device included in a system for providing a life support complex solution according to one embodiment of the present invention.

Referring to FIG. 12, a biosignal measurement device 1200 includes a biosignal monitor 1210 and a controller 1230.

According to one embodiment of the present invention, the biosignal measurement device 1200 is attached to the upper part of or near the heart of an applicant to measure heart condition-related data from the applicant, or is worn as a wearable device in the form of a band on the user's wrist to measure heart condition-related data.

In addition, the biosignal measurement device 1200 may include a 3D depth camera for obtaining 3D depth images for daily life pattern analysis, a smart band that may be worn on at least one of the applicant's ear, neck, and wrist, and a sensor device for detecting a heart condition.

For example, the biosignal monitor 1210 may measure biosignals including at least one of a 3D depth image, an electrocardiogram signal, a pulse wave signal, a body temperature signal, and a motion signal from an applicant, and may output monitoring information including the measured biosignals through an artificial intelligence encoder.

According to one embodiment of the present invention, the biosignal monitor 1210 may encode and compress heart condition information according to change in an applicant's heart condition and movement state information according to change in applicant's movement through an artificial intelligence encoder and output the information.

According to one embodiment of the present invention, the biosignal monitor 1210 may monitor a body reaction and a body temperature as biosignals by physical activity measurement (Actigraph) measured from at least one of an ear, a neck, and a wrist, and may encode and output motion signals according to the body reaction and a body temperature signal through an artificial intelligence encoder.

For example, the biosignal monitor 1210 may monitor neural responses as biosignals by photoplethysmography (PPG) measured from at least one of an ear, a neck, and a wrist, and may encode and output autonomic neural information according to the neural responses through an artificial intelligence encoder.

For example, the controller 1230 may transmit the monitoring information to the server through a gateway located nearby using short-range wireless communication.

According to one embodiment of the present invention, the controller 1230 may extract electrocardiogram signals included in monitoring information, may extract morphological information as feature information by converting extracted electrocardiogram signals into a time-standardized image based on a pre-stored artificial intelligence machine learning algorithm, may determine a plurality of cardiac abnormality type models using the extracted feature information, may calculate classification accuracy for the determined cardiac abnormality type models, and provide monitoring information to the server so that a cardiovascular disease of the applicant is determined using the determined cardiac abnormality type models and public cardiovascular disease data based on the calculated accuracy.

For example, the controller 1230 may simulate data traffic generated when at least one of a 3D depth image, an electrocardiogram signal, a motion signal, a body temperature signal, and a pulse wave signal is measured, and may determine the operating state of the biosignal measurement device based on the simulation.

For example, the controller 1230 may periodically check a battery state, determine a low battery state, and provide alarm information.

According to one embodiment of the present invention, the controller 1230 may provide monitoring information to the server so that emergency states including cardiac arrest and a fall of an applicant are detected based on a 3D depth image, an electrocardiogram signal, a motion signal, a body temperature signal, and a pulse wave signal.

According to one embodiment of the present invention, the biosignal measurement device 1200 may further include an artificial intelligence processor 1220.

For example, the artificial intelligence processor 1220 may extract electrocardiogram signals included in output monitoring information from the biosignal monitor 1210, extract morphological information as feature information by converting the extracted electrocardiogram signals into a time-standardized image based on a pre-stored artificial intelligence machine learning algorithm, determine a plurality of cardiac abnormality type models using the extracted feature information, calculate classification accuracy for the determined cardiac abnormality type models, and determine a cardiovascular disease of a user using the determined cardiac abnormality type models and public cardiovascular disease data based on the calculated accuracy.

For example, the artificial intelligence processor 1220 may automatically calculate the classification accuracy by comparing an open data set and cardiac abnormality type models based on an artificial intelligence learning technique.

For example, the artificial intelligence processor 1220 may include a convolutional neural network layer and a bidirectional long short-term memory (BLSTM) layer.

According to one embodiment of the present invention, the artificial intelligence processor 1220 has the same information processing function as the artificial intelligence processor of the server to be described with reference to FIG. 8, and may perform learning and analysis based on an artificial intelligence machine learning algorithm.

That is, the biosignal measurement device 1200 according to one embodiment of the present invention may transmit monitoring information for classifying left bundle branch block, right bundle branch block, premature atrial contraction, and premature ventricular contraction related to arrhythmia to the server.

In addition, the biosignal measurement device 1200 according to one embodiment of the present invention may perform machine learning of monitoring information to classify left bundle branch block, right bundle branch block, premature atrial contraction, and premature ventricular contraction related to arrhythmia, and may provide the classified information.

Accordingly, the present invention may provide a life support complex solution that transmits emergency information and basic biosignal information to medical staff and emergency centers of nursing hospitals when an emergency such as cardiac arrest or a fall accident is detected, allows external organizations to receive analysis data in real time, and prepares for emergency states of applicants.

In addition, the present invention may reduce the number of false alarms occurring in a ward by accurately measuring and analyzing the current condition of a patient, and thus may improve the work efficiency of medical staff and the prognosis of a patient.

FIG. 13 is a diagram for explaining a method of operating a system for providing a life support complex solution according to one embodiment of the present invention.

FIG. 13 illustrates an embodiment in which biosignals measured using a biosignal measurement device in a system for providing a life support complex solution according to one embodiment of the present invention are learned and analyzed using a pre-stored artificial intelligence algorithm, and at least one of information about a cardiovascular disease of an applicant and whether an applicant is in an emergency state and change information of the biosignals is feed-back to a user terminal to provide a life support complex solution.

Referring to FIG. 13, in the method of operating a system for providing a life support complex solution according to one embodiment of the present invention, in step 1301, the biosignals of an applicant are measured.

That is, according to the method of operating a system for providing a life support complex solution, biosignals including an electrocardiogram signal, a motion signal, a body temperature signal, and a pulse wave signal are measured using a biosignal measurement device attached to the upper side of the applicant's heart and a biosignal measurement device worn on at least one of an ear, a neck, and a wrist of the applicant.

In the method of operating a system for providing a life support complex solution according to one embodiment of the present invention, in step 1302, monitoring information including the biosignals measured in step 1301 is transmitted to the server.

That is, according to the method of operating a system for providing a life support complex solution, biosignals including an electrocardiogram signal, a motion signal, a body temperature signal, and a pulse wave signal are encoded and compressed using an artificial intelligence encoder to generate monitoring information, and the generated monitoring information is transmitted to a server through an adjacent gateway.

According to the method of operating a system for providing a life support complex solution, in step 1303, cardiac abnormality type models are determined based on an artificial intelligence machine learning algorithm, and a degree of classification based on the cardiac abnormality type models is calculated.

Specifically, according to the method of operating a system for providing a life support complex solution, normalized signals generated based on the time domain of electrocardiogram signals may be converted into a time-standardized image, a pre-stored artificial intelligence machine learning algorithm-based weight may be applied to the converted image to generate a compressed signal, a reconstructed signal may be generated from the compressed signal using the applied weight, and feature information corresponding to the morphological feature of the electrocardiogram signals may be extracted by performing machine learning of the weight so that a difference between the generated normalized signal and the generated reconstructed signal falls within a preset threshold range.

In addition, according to the method of operating a system for providing a life support complex solution, machine learning of the extracted feature information may be performed to determine a plurality of cardiac abnormality type models as a tachycardia model, a bradycardia model, an atrial fibrillation model, a left bundle branch block model, a right bundle branch block model, a premature atrial contraction model, a premature ventricular contraction model, a normal heart condition model, and a cardiac arrest model.

In addition, according to the method of operating a system for providing a life support complex solution, classification accuracy for a plurality of cardiac abnormality type models is calculated.

That is, according to the method of operating a system for providing a life support complex solution, depending on the determination results of a plurality of cardiac abnormality type models, classification accuracy for the cardiac abnormality type models may be quantified.

Specifically, according to the method of operating a system for providing a life support complex solution, each of a plurality of cardiac abnormality type models may be classified into four cases including a true positive (TP) case in which cardiac abnormality is classified as cardiac abnormality, a false negative (FN) case in which cardiac abnormality is classified as normal, a false positive (FP) case in which normal is classified as cardiac abnormality, and a true negative (TN) case in which normal is classified as normal.

In addition, in the method of operating a system for providing a life support complex solution, classification accuracy is calculated based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

In addition, according to the method of operating a system for providing a life support complex solution, when classification accuracy of cardiac abnormality types related to tachycardia, bradycardia, atrial fibrillation, left bundle branch block, right bundle branch block, premature atrial contraction, and premature ventricular contraction with the numerical value of the calculated classification accuracy is higher than a threshold value, the type of cardiac abnormality may be determined as a least one of tachycardia, bradycardia, atrial fibrillation, left bundle branch block, right bundle branch block, premature atrial contraction, and premature ventricular contraction, an emergency state related to cardiac arrest may be determined, and an artifact removal rate may be determined based on artifact removal probability.

According to the method of operating a system for providing a life support complex solution according to one embodiment of the present invention, in step 1304, a cardiovascular disease is determined using the accuracy, the cardiac abnormality type models, and public cardiovascular disease data.

That is, according to the method of operating a system for providing a life support complex solution, based on the accuracy calculated in step 1303, the cardiac abnormality type model determined in step 1303 and public cardiovascular disease data as public data may be compared to determine a cardiovascular disease of an applicant wearing the biosignal measurement device.

According to the method of operating a system for providing a life support complex solution according to one embodiment of the present invention, in step 1305, change information of biosignals and information about a cardiovascular disease and an emergency state may be fed back to a user terminal.

According to the method of operating a system for providing a life support complex solution according to one embodiment of the present invention, in step 1306, feedback information may be displayed, and an alarm feedback may be provided according to the feedback information.

That is, according to the method of operating a system for providing a life support complex solution according to one embodiment of the present invention, information including at least one of information about the determined cardiovascular disease and the emergency state and change information of the biosignals may be output, and prescription information generated according to the information output to a medical staff terminal may also be updated in a guardian terminal and an emergency center terminal.

In addition, according to the method of operating a system for providing a life support complex solution according to one embodiment of the present invention, based on information about the determined cardiovascular disease and the emergency state and change information of the biosignals, at least one of a nursing management service, a disease data management service, a disease data visualization service, a disease data statistical service, and an emergency push notification service of an applicant may be provided.

Accordingly, the present invention may detect the heart condition of a patient for heart condition analysis for real-time arrhythmia detection, biosignal quality management to improve signal analysis reliability, and assessment of major cardiovascular diseases for early disease management.

In addition, the present invention may detect major cardiac abnormalities such as tachycardia, bradycardia, atrial fibrillation, left bundle branch block, right bundle branch block, premature atrial contraction, premature ventricular contraction, and cardiac arrest by analyzing, based on a pre-stored artificial intelligence algorithm, biosignals measured by a biosignal measurement device that is attached to a patient and detects the heart condition of the patient.

In addition, the present invention may improve the measurement accuracy of biosignals measured by a biosignal measurement device that is attached to a patient and detects the condition of the patient by learning and evaluating the measurement accuracy of the biosignals by calculating cardiac dysfunction classification accuracy, emergency state classification accuracy, and artifact signal detection accuracy using a pre-stored artificial intelligence algorithm and an open data set.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

The methods according to the embodiments of the present invention may be implemented in the form of a program command that can be executed through various computer means and recorded in a computer-readable medium. The computer-readable medium can store program commands, data files, data structures or combinations thereof. The program commands recorded in the medium may be specially designed and configured for the present invention or be known to those skilled in the field of computer software. Examples of a computer-readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands Examples of the program commands include machine language code created by a compiler and high-level language code executable by a computer using an interpreter and the like. The hardware devices described above may be configured to operate as one or more software modules to perform the operations of the embodiments, and vice versa.

Although the present invention has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

The invention claimed is:

1. A server that is linked to a sensor device for detecting a heart condition and provides user condition information, the server comprising:
    a monitoring information collector for collecting monitoring information comprising biosignals comprising electrocardiogram signals measured from a user;
    a signal extractor for extracting the electrocardiogram signals comprised in the collected monitoring information;
    an artificial intelligence processor configured to execute instructions; and
    a memory storing the instructions, wherein execution of the instructions configures the artificial intelligence processor to:
        extract morphological information as feature information by converting the extracted electrocardiogram signals into a time-standardized image based on a pre-stored artificial intelligence machine learning algorithm;
        determining a plurality of cardiac abnormality type models using the extracted feature information;
        calculating classification accuracy for the determined cardiac abnormality type models; and
        determine a cardiovascular disease of the user using the determined cardiac abnormality type models and public cardiovascular disease data based on the calculated accuracy; and
    a controller for controlling to provide the determined cardiovascular disease to a user terminal.

2. The server according to claim 1, wherein the artificial intelligence processor is further configured to:
    generate a normalized signal based on a time domain of the extracted electrocardiogram signals, converts the generated normalized signal into the time-standardized image;
    generate a compressed signal by applying the pre-stored artificial intelligence machine learning algorithm-based weight to the converted image;
    generate a reconstructed signal from the compressed signal using the applied weight; and
    extract morphological information of the electrocardiogram signals as the feature information by performing machine learning of the weight so that a difference between the generated normalized signal and the generated reconstructed signal falls within a preset threshold range.

3. The server according to claim 1, wherein the artificial intelligence processor is further configured to:
    perform machine learning of the feature information to determine the cardiac abnormality type models as at least one model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

4. The server according to claim 3, wherein the artificial intelligence processor is further configured to:
use an open data set, one or more model of the tachycardia model, the bradycardia model, the atrial fibrillation model, the left bundle branch block model, the right bundle branch block model, the premature atrial contraction model, and the premature ventricular contraction model, and the normal heart condition model to classify a true positive (TP) case in which cardiac abnormality is classified as the cardiac abnormality, a false negative (FN) case in which the cardiac abnormality is classified as normal, a false positive (FP) case in which the normal is classified as the cardiac abnormality, and a true negative (TN) case in which the normal is classified as the normal; and
calculate classification accuracy for at least one or more of the tachycardia model, the bradycardia model, the atrial fibrillation model, the left bundle branch block model, the right bundle branch block model, the premature atrial contraction model, and the premature ventricular contraction model based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

5. The server according to claim 3, wherein the artificial intelligence processor is further configured to:
use an open data set, the cardiac arrest model, and the normal heart condition model to classify a true positive (TP) case in which a cardiac arrest section is classified as the cardiac arrest section, a false negative (FN) case in which the cardiac arrest section is classified as a normal section, a false positive (FP) case in which the normal section is classified as the cardiac arrest section, and a true negative (TN) case in which the normal section is classified as the normal section, and calculates emergency state classification accuracy based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

6. The server according to claim 3, wherein the artificial intelligence processor is further configured to classify:
a true positive (TP) case in which an artifact signal is classified as the artifact signal, a false negative (FN) case in which the artifact signal is classified as a normal signal, a false positive (FP) case in which the normal signal is classified as the artifact signal, and
a true negative (TN) case in which the normal signal is classified as the normal signal; and
calculate artifact removal accuracy based on a ratio of a combination of a numerical value of the true positive (TP) case and a numerical value of the true negative (TN) case to a combination of a numerical value of the true positive (TP) case, a numerical value of the false negative (FN) case, a numerical value of the false positive (FP) case, and a numerical value of the true negative (TN) case.

7. The server according to claim 6, wherein, after the electrocardiogram signals are measured, the controller calculates the number of the measured electrocardiogram signals and compares the calculated number of the electrocardiogram signals with a threshold value to confirm a data reception state of the electrocardiogram signals.

8. The server according to claim 6, wherein the user terminal provides an analysis result related to the determined cardiovascular disease through a display.

9. A sensor device for detecting a heart condition, comprising:
a biosignal monitor for measuring biosignals comprising electrocardiogram signals from a user and outputting monitoring information comprising the measured biosignals through an artificial intelligence encoder;
an artificial intelligence processor configured to execute instructions; and
a memory storing the instructions, wherein execution of the instructions configures the artificial intelligence processor to:
extract electrocardiogram signals comprised in the output monitoring information;
extract morphological information as feature information by converting the extracted electrocardiogram signals into a time-standardized image based on a pre-stored artificial intelligence machine learning algorithm;
determine a plurality of cardiac abnormality type models using the extracted feature information;
calculate classification accuracy for the determined cardiac abnormality type models, models; and
determine a cardiovascular disease of the user using the determined cardiac abnormality type models and public cardiovascular disease data based on the calculated accuracy.

10. The sensor device according to claim 9, wherein the artificial intelligence processor is further configured to:
simulate data traffic generated when measuring the electrocardiogram signals; and
determine an operating state of the sensor device for detecting a heart condition based on the simulation.

11. The sensor device according to claim 9, wherein the artificial intelligence processor is further configured to:
perform machine learning of the feature information to determine the cardiac abnormality type models as one or more of a model of a tachycardia model, a bradycardia model, an atrial fibrillation model, a left bundle branch block model, a right bundle branch block model, a premature atrial contraction model, a premature ventricular contraction model, a cardiac arrest model, and a normal heart condition model.

12. The sensor device according to claim 9, wherein the biosignal monitor further measures at least one of a motion signal and a body temperature signal from the user, and outputs monitoring information further comprising the motion signal and the body temperature signal through an artificial intelligence encoder.

13. The sensor device according to claim 12, wherein the artificial intelligence processor is further configured to:
detect emergency states comprising cardiac arrest and a fall of the user based on the measured electrocardiogram signals and the measured motion signals.

14. A method of monitoring a heart condition using the server of claim 1, the method comprising:

measuring electrocardiogram signals from a user by the sensor device for detecting a heart condition;

extracting, by the server, morphological information as feature information by converting the measured electrocardiogram signals into a time-standardized image;

determining, by the server, a plurality of cardiac abnormality type models by performing machine learning of the extracted feature information;

calculating classification accuracy for the determined cardiac abnormality type models by the server; and determining, by the server, a cardiovascular disease of the user using the determined cardiac abnormality type models and public cardiovascular disease data based on the calculated accuracy.

15. A system for providing a life support complex solution, comprising:

a gateway for transmitting monitoring information comprising biosignals comprising at least one of an electrocardiogram signal, a motion signal, a body temperature signal, and a pulse wave signal of an applicant to a server; and a server for extracting electrocardiogram signals of the biosignals from the transmitted monitoring information, extracting morphological information as feature information by converting the extracted electrocardiogram signals into a time-standardized image based on a pre-stored artificial intelligence machine learning algorithm, determining a plurality of cardiac abnormality type models using the extracted feature information, calculating classification accuracy for the determined cardiac abnormality type models, determining a cardiovascular disease of the applicant and whether the applicant is in an emergency state using the determined cardiac abnormality type models and public cardiovascular disease data based on the calculated accuracy, and feeding back information about the determined cardiovascular disease and whether the applicant is in an emergency state and change information of the biosignals to a user terminal.

16. The system according to claim 15, wherein the user terminal comprises at least one of a medical staff terminal, a guardian terminal, and an emergency center terminal, the user terminal outputs at least one of information about the determined cardiovascular disease and whether the applicant is in an emergency state and change information of the biosignals, and prescription information generated according to information output to the medical staff terminal is also updated in the guardian terminal and the emergency center terminal.

17. The system according to claim 16, wherein, based on information about the determined cardiovascular disease and whether the applicant is in an emergency state and change information of the biosignals, the user terminal provides at least one of a nursing management service, a disease data management service, a disease data visualization service, a disease data statistical service, and an emergency push notification service of the applicant.

18. The system according to claim 15, further comprising a biosignal monitor for measuring biosignals comprising at least one of a 3D depth image, an electrocardiogram signal, a motion signal, a body temperature signal, and a pulse wave signal from the applicant and outputting monitoring information comprising the measured biosignals through an artificial intelligence encoder; and a biosignal measurement device comprising a controller for controlling to transmit the output monitoring information to the server through the gateway using short-range wireless communication.

19. The system according to claim 18, wherein the biosignal monitor monitors a neural response by photoplethysmography (PPG) measured from at least one of an ear, a neck, and a wrist as the biosignals, and encodes and outputs autonomic neural information according to the neural response through an artificial intelligence encoder.

20. A method of operating the system of claim 15, wherein the method comprises a step of measuring, by a biosignal measurement device, biosignals comprising at least one of an electrocardiogram signal, a motion signal, a body temperature signal, and a pulse wave signal from an applicant;

transmitting, by the biosignal measurement device, monitoring information comprising the measured biosignals to a server through a gateway;

extracting, by the server, electrocardiogram signals of the biosignals from the transmitted monitoring information and extracting morphological information as feature information by converting the extracted electrocardiogram signals into a time-standardized image based on a pre-stored artificial intelligence machine learning algorithm;

determining, by the server, a plurality of cardiac abnormality type models using the extracted feature information;

calculating classification accuracy for the determined cardiac abnormality type models by the server;

determining, by the server, a cardiovascular disease of the applicant and whether the applicant is in an emergency state using the determined cardiac abnormality type models and public cardiovascular disease data based on the calculated accuracy; and feeding back, by the server, information about the determined cardiovascular disease and whether the applicant is in an emergency state and change information of the biosignals to a user terminal.

* * * * *